US010336990B2

(12) United States Patent
Kim et al.

(10) Patent No.: US 10,336,990 B2
(45) Date of Patent: Jul. 2, 2019

(54) HELICOBACTER PYLORI α-1,3 FUCOSYLTRANSFERASE GENE AND PROTEIN WITH IMPROVED SOLUBLE PROTEIN EXPRESSION AND ACTIVITY, AND THEREOF APPLICATION FOR SYNTHESIS OF α-1,3 FUCOSYLOLIGOSACCHARIDE

(71) Applicant: SEOUL NATIONAL UNIVERSITY R&DB FOUNDATION, Seoul (KR)

(72) Inventors: Byung Gee Kim, Seoul (KR); Yun Hee Choi, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/322,072

(22) PCT Filed: Jun. 22, 2015

(86) PCT No.: PCT/KR2015/006272
§ 371 (c)(1),
(2) Date: Dec. 23, 2016

(87) PCT Pub. No.: WO2015/199387
PCT Pub. Date: Dec. 30, 2015

(65) Prior Publication Data
US 2017/0247668 A1  Aug. 31, 2017

(30) Foreign Application Priority Data
Jun. 23, 2014  (KR) .................. 10-2014-0076720

(51) Int. Cl.
*C12N 9/10*  (2006.01)
*C12N 1/14*  (2006.01)
(Continued)

(52) U.S. Cl.
CPC ............ *C12N 9/1051* (2013.01); *C12N 1/14* (2013.01); *C12N 1/20* (2013.01); *C12P 19/00* (2013.01);
(Continued)

(58) Field of Classification Search
None
See application file for complete search history.

(56) References Cited

U.S. PATENT DOCUMENTS 7,214,517 B2   5/2007  Kamada et al.
2002/0068347 A1  6/2002  Taylor et al.
(Continued)

FOREIGN PATENT DOCUMENTS

EP   2439264 A1   4/2012
WO   2015/199387 A2   12/2015

OTHER PUBLICATIONS

Geneseq Accession No. ABG30885, published Aug. 29, 2003.*
PCT/KR2015/006272 International Search Report and Written Opinion dated Jan. 18, 2016, 19 pages.
PCT/KR2015/006272 International Preliminary Report on Patentability dated Dec. 27, 2016, 23 pages.
(Continued)

*Primary Examiner* — Richard C Ekstrom
(74) *Attorney, Agent, or Firm* — Linda B. Huber; Nixon Peabody LLP

(57) ABSTRACT

The present invention provides an α-1,3 fucosyltransferase mutant having an increased expression level of soluble protein and increased activity, a DNA encoding the α-1,3 fucosyltransferase mutant, a recombinant vector comprising the DNA encoding the α-1,3 fucosyltransferase mutant, a host cell transformed with the recombinant DNA vector, an extract of the host cell, a method for producing 3-fucosyloligosaccharide, a method for preparing an α-1,3 fucosyltransferase mutant, and a method for screening an α-1,3
(Continued)

fucosyltransferase mutant. The α-1,3 fucosyltransferase mutant of the present invention has a significantly increased soluble protein expression level and activity.

17 Claims, 3 Drawing Sheets

Specification includes a Sequence Listing.

(51) Int. Cl.
  *C12N 1/20* (2006.01)
  *C12P 19/00* (2006.01)
  *C12P 19/18* (2006.01)
  *C12Q 1/48* (2006.01)

(52) U.S. Cl.
  CPC ............... *C12P 19/18* (2013.01); *C12Q 1/48* (2013.01); *C12Y 204/01065* (2013.01); *G01N 2333/91102* (2013.01)

(56) References Cited

U.S. PATENT DOCUMENTS

| 2005/0164338 A1 | 7/2005 | Simala-Grant et al. |
| 2013/0217068 A1 | 8/2013 | Parkot et al. |
| 2017/0226547 A1* | 8/2017 | Merighi ................. C12P 19/00 |
| 2017/0247668 A1* | 8/2017 | Kim ........................ C12P 19/18 |

OTHER PUBLICATIONS

Albesa-Jove et al., Structure-Function Relationships of Membrane-Associated GT-B Glycosyltransferases, 2013, Glycobiology, vol. 24(2), pp. 108-124.
NCBI GenBank Accession No. WP_000487428: Fucosyltransferase [Helicobacter Pylori], 2013.
Sun et al., Structure and Mechanism of Helicobacter Pylori Fucosyltransferase. A Basis for Lipopolysaccharide Variation and Inhibitor Design, 2007, Journal of Biological Chemistry, vol. 282(13), pp. 9973-9982.

* cited by examiner

SEQUENCE LISTING

<160> NUMBER OF SEQ ID NOS: 27

<210> SEQ ID NO 1
<211> LENGTH: 380
<212> TYPE: PRT
<213> ORGANISM: helicobacter pylori

<400> SEQUENCE: 1

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
            115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
            195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
            275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
            355                 360                 365

```
Leu Arg Val Asn Tyr Asp Asp Leu Arg Val Asn Tyr
    370                 375                 380
```

<210> SEQ ID NO 2
<211> LENGTH: 373
<212> TYPE: PRT
<213> ORGANISM: helicobacter pylori

<400> SEQUENCE: 2

```
Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
        355                 360                 365
```

Leu Arg Val Asn Tyr
    370

<210> SEQ ID NO 3
<211> LENGTH: 366
<212> TYPE: PRT
<213> ORGANISM: helicobacter pylori

<400> SEQUENCE: 3

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile

<210> SEQ ID NO 4
<211> LENGTH: 1119
<212> TYPE: DNA
<213> ORGANISM: helicobacter pylori

<400> SEQUENCE: 4

```
atgttccaac cacttttaga cgcatttatc gagtcggcat caattgagaa aatggcatcg      60
aagagcccgc caccgccgtt gaagatcgcc gtcgctaact ggtggggcga cgaagagatc     120
aaagagttca agaaatctgt gctgtatttc atcctgtccc agcgctatgc gattacgctg     180
caccaaaatc cgaacgagtt cagcgacctg gttctgtcta acccgctggg cgcagcgcgt     240
aagattctga gctaccagaa taccaaacgt gttttctaca ccggtgaaaa cgaaagcccg     300
aacttcaact tgtttgatta cgctatcggt tttgatgaac tggatttcaa tgatcgctat     360
ctgcgtatgc cgctgtacta cgcgcatctg cactataaag ccgagctggt caacgacact     420
accgcgccat ataagctgaa agataatagc ctgtatgcct tgaagaaacc tagccaccac     480
ttcaaagaaa accacccgaa tctgtgcgca gtggttaatg atgaaagcga tctgctgaaa     540
cgtggttttg cgagctttgt cgcaagcaac gccaatgccc cgatgcgtaa cgcttttttac     600
gacgcgctga acagcattga gccggtgacc ggtggcggta gcgtgcgcaa tacgttgggc     660
tacaaagtcg gtaataagag cgagttcctg agccagtaca agtttaatct gtgttttgag     720
aacagccaag gctatggtta cgttaccgag aagatcctgg acgcgtactt ctctcacacc     780
attccgatct attggggcag cccgtccgtt gcgaaagact tcaatccgaa atcctttgtg     840
aatgtccacg acttcaataa cttttgatgag gcgattgatt acattaagta tctgcacacg     900
catccgaatg cgtacttgga catgctgtat gaaaaacccgc tgaacaccct ggacggtaag     960
gcgtactttt accaggacct gagcttcaag aaaatcctgg acttttttcaa aaccatcctg    1020
gaaaacgata cgattttacca caagttcagc acgagcttta tgtgggaata tgatttgcat    1080
aagccgctgg ttagcattga cgatctgcgt gtgaattac                            1119
```

<210> SEQ ID NO 5
<211> LENGTH: 1119
<212> TYPE: DNA
<213> ORGANISM: helicobacter pylori

<400> SEQUENCE: 5

```
atgttccaac ccctattaga cgcctttata gaaagcgctt ccattgaaaa aatggcctct      60
aaatctcccc cccccccct aaaaatcgct gtggcgaatt ggtggggaga tgaagaaatt     120
aaagaatta aaaagagcgt tctttatttt atcctaagcc aacgctacgc aatcaccctc     180
caccaaaacc ccaatgaatt ttcagatcta gttcttagca atcctcttgg agcggctaga     240
aagattttat cttatcaaaa cactaaacga gtgttttaca ccggtgaaaa cgaatcacct     300
aatttcaacc tctttgatta cgccataggc tttgatgaat tggattttaa tgatcgttat     360
ttgagaatgc ctttgtatta tgcccatttg cactataaag ccgagcttgt taatgacacc     420
actgcgccct acaaactcaa agacaacagc ctttatgctt taaaaaaacc ctctcatcat     480
tttaaagaaa accaccctaa tttgtgcgca gtagtgaatg atgagagcga tcttttaaaa     540
agagggtttg ccagttttgt agcgagcaac gctaacgctc ctatgaggaa cgcttttttat     600
gacgctctaa attccataga gccagttact ggggaggaa gtgtgagaaa cacttttaggc     660
tataaggttg gaaacaaaag cgagttttta agccaataca agttcaatct ctgttttgaa     720
```

```
aactcgcaag gttatggcta tgtaaccgaa aaaatccttg atgcgtattt tagccatacc    780
attcctattt attggggag tcccagcgtg gcgaaagatt ttaaccctaa aagttttgtg    840
aatgtgcatg atttcaacaa ctttgatgaa gcgattgatt atatcaaata cctgcacacg   900
cacccaaacg cttatttaga catgctctat gaaaacccct taaacaccct tgatgggaaa   960
gcttactttt accaagattt gagttttaaa aaaatcctag attttttttaa aacgatttta  1020 gaaaacgata cgatttatca caattctca acatctttca tgtgggagta cgatctgcat    1080
aagccgttag tatccattga tgatttgagg gttaattat                         1119
```

<210> SEQ ID NO 6
<211> LENGTH: 373
<212> TYPE: PRT
<213> ORGANISM: helicobacter pylori

<400> SEQUENCE: 6

```
Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300
```

```
Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
        355                 360                 365

Leu Arg Val Asn Tyr
    370

<210> SEQ ID NO 7
<211> LENGTH: 373
<212> TYPE: PRT
<213> ORGANISM: helicobacter pylori

<400> SEQUENCE: 7

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

Glu Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
```

```
                  290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
            355                 360                 365

Leu Arg Val Asn Tyr
        370

<210> SEQ ID NO 8
<211> LENGTH: 373
<212> TYPE: PRT
<213> ORGANISM: helicobacter pylori

<400> SEQUENCE: 8

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Ile Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285
```

-continued

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
            355                 360                 365

Leu Arg Val Asn Tyr
    370

<210> SEQ ID NO 9
<211> LENGTH: 373
<212> TYPE: PRT
<213> ORGANISM: helicobacter pylori

<400> SEQUENCE: 9

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Phe Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

```
Asp Glu Ala Ile Asp Tyr Ile Lys Tyr Leu His Thr His Pro Asn Ala
            290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
            355                 360                 365

Leu Arg Val Asn Tyr
            370

<210> SEQ ID NO 10
<211> LENGTH: 373
<212> TYPE: PRT
<213> ORGANISM: helicobacter pylori

<400> SEQUENCE: 10

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
            115                 120                 125

Glu Leu His Tyr Lys Ala Glu Leu Val Asn Asp Thr Thr Ala Pro Tyr
130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
            195                 200                 205

Val Thr Gly Gly Gly Ser Val Arg Asn Thr Leu Gly Tyr Lys Val Gly
            210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
```

```
                   275                 280                 285
Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Ile Leu Asp Phe Phe
                325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
            355                 360                 365

Leu Arg Val Asn Tyr
            370

<210> SEQ ID NO 11
<211> LENGTH: 373
<212> TYPE: PRT
<213> ORGANISM: helicobacter pylori

<400> SEQUENCE: 11

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
        115                 120                 125

His Leu His Ile Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Val Ala Lys
            260                 265                 270
```

Asp Phe Asn Pro Lys Ser Phe Val Asn Val His Asp Phe Asn Asn Phe
                275                 280                 285

Asp Glu Ala Ile Asp Tyr Ile Lys Tyr Leu His Thr His Pro Asn Ala
        290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
        355                 360                 365

Leu Arg Val Asn Tyr
    370

<210> SEQ ID NO 12
<211> LENGTH: 373
<212> TYPE: PRT
<213> ORGANISM: helicobacter pylori

<400> SEQUENCE: 12

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Phe Val Leu
            35                  40                  45

Tyr Phe Ile Leu Ser Gln Arg Tyr Ala Ile Thr Leu His Gln Asn Pro
50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

-continued

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
        355                 360                 365

Leu Arg Val Asn Tyr
        370

<210> SEQ ID NO 13
<211> LENGTH: 373
<212> TYPE: PRT
<213> ORGANISM: helicobacter pylori

<400> SEQUENCE: 13

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
        115                 120                 125

Glu Leu His Ile Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys

```
                     260                 265                 270
Asp Phe Asn Pro Lys Ser Phe Val Asn Val His Asp Phe Asn Phe
            275                 280                 285
Asp Glu Ala Ile Asp Tyr Ile Lys Tyr Leu His Thr His Pro Asn Ala
            290                 295                 300
Tyr Leu Asp Met Leu Tyr Glu Asn Pro Leu Asn Thr Leu Asp Gly Lys
305                 310                 315                 320
Ala Tyr Phe Tyr Gln Asp Leu Ser Phe Lys Lys Ile Leu Asp Phe Phe
            325                 330                 335
Lys Thr Ile Leu Glu Asn Asp Thr Ile Tyr His Lys Phe Ser Thr Ser
            340                 345                 350
Phe Met Trp Glu Tyr Asp Leu His Lys Pro Leu Val Ser Ile Asp Asp
            355                 360                 365
Leu Arg Val Asn Tyr
            370

<210> SEQ ID NO 14
<211> LENGTH: 373
<212> TYPE: PRT
<213> ORGANISM: helicobacter pylori

<400> SEQUENCE: 14

Met Phe Gln Pro Leu Leu Asp Ala Phe Ile Glu Ser Ala Ser Ile Glu
1               5                   10                  15
Lys Met Ala Ser Lys Ser Pro Pro Pro Leu Lys Ile Ala Val Ala
            20                  25                  30
Asn Trp Trp Gly Asp Glu Glu Ile Lys Glu Phe Lys Lys Phe Val Leu
            35                  40                  45
Tyr Phe Ile Leu Ser Gln Arg Tyr Ala Ile Thr Leu His Gln Asn Pro
        50                  55                  60
Asn Glu Phe Ser Asp Leu Val Leu Ser Asn Pro Leu Gly Ala Ala Arg
65                  70                  75                  80
Lys Ile Leu Ser Tyr Gln Asn Thr Lys Arg Val Phe Tyr Thr Gly Glu
            85                  90                  95
Asn Glu Ser Pro Asn Phe Asn Leu Phe Asp Tyr Ala Ile Gly Phe Asp
            100                 105                 110
Glu Leu Asp Phe Asn Asp Arg Tyr Leu Arg Met Pro Leu Tyr Tyr Asn
            115                 120                 125
Glu Leu His Tyr Lys Ala Glu Leu Val Asn Asp Thr Thr Ala Pro Tyr
            130                 135                 140
Lys Leu Lys Asp Asn Ser Leu Tyr Ala Leu Lys Lys Pro Ser His His
145                 150                 155                 160
Phe Lys Glu Asn His Pro Asn Leu Cys Ala Val Val Asn Asp Glu Ser
            165                 170                 175
Asp Leu Leu Lys Arg Gly Phe Ala Ser Phe Val Ala Ser Asn Ala Asn
            180                 185                 190
Ala Pro Met Arg Asn Ala Phe Tyr Asp Ala Leu Asn Ser Ile Glu Pro
            195                 200                 205
Val Thr Gly Gly Gly Ser Val Arg Asn Thr Leu Gly Tyr Lys Val Gly
            210                 215                 220
Asn Lys Ser Glu Phe Leu Ser Gln Tyr Lys Phe Asn Leu Cys Phe Glu
225                 230                 235                 240
Asn Ser Gln Gly Tyr Gly Tyr Val Thr Glu Lys Ile Leu Asp Ala Tyr
            245                 250                 255
```

```
Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
            275                 280                 285

Asp Glu Ala Ile Asp Tyr Ile Lys Tyr Leu His Thr His Pro Asn Ala
        290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
            325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
            355                 360                 365

Leu Arg Val Asn Tyr
            370

<210> SEQ ID NO 15
<211> LENGTH: 373
<212> TYPE: PRT
<213> ORGANISM: helicobacter pylori

<400> SEQUENCE: 15

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Phe Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65              70                  75                  80

Lys Ile Leu Ser Tyr Gln Asn Thr Lys Arg Val Phe Tyr Thr Gly Glu
            85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
            115                 120                 125

His Leu His Ile Lys Ala Glu Leu Val Asn Asp Thr Thr Ala Pro Tyr
        130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
            165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
            210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
            245                 250                 255
```

```
Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
        355                 360                 365

Leu Arg Val Asn Tyr
    370

<210> SEQ ID NO 16
<211> LENGTH: 373
<212> TYPE: PRT
<213> ORGANISM: helicobacter pylori

<400> SEQUENCE: 16

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Phe Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Leu Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Asn
        115                 120                 125

Glu Leu His Ile Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
```

```
                245             250             255
Phe Ser His Thr Ile Pro Ile Tyr Trp Gly Ser Pro Ser Val Ala Lys
        260                 265                 270

Asp Phe Asn Pro Lys Ser Phe Val Asn Val His Asp Phe Asn Asn Phe
    275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
            325                 330                 335

Lys Thr Ile Leu Glu Asn Asp Thr Ile Tyr His Lys Phe Ser Thr Ser
                340                 345                 350

Phe Met Trp Glu Tyr Asp Leu His Lys Pro Leu Val Ser Ile Asp Asp
            355                 360                 365

Leu Arg Val Asn Tyr
    370

<210> SEQ ID NO 17
<211> LENGTH: 1119
<212> TYPE: DNA
<213> ORGANISM: helicobacter pylori

<400> SEQUENCE: 17
atgttccaac cacttttaga cgcatttatc gagtcggcat caattgagaa atggcatcg      60 aagagcccgc caccgccgtt gaagatcgcc gtcgctaact ggtggggcga cgaagagatc    120
aaagagttca gaaatctgt gctgtatttc atcctgtccc agcgctatgc gattacgctg     180
caccaaaatc cgaacgagtt cagcgacctg gttctgtcta acccgctggg cgcagcgcgt    240
aagattctga gctaccagaa taccaaacgt gttttctaca ccggtgaaaa cgaaagcccg    300
aacttcaact tgtttgatta cgctatcggt tttgatgaac tggatttcaa tgatcgctat    360
ctgcgtatgc cgctgtacta caatcatctg cactataaag ccgagctggt caacgacact    420
accgcgccat ataagctgaa agataatagc ctgtatgcct tgaagaaacc tagccaccac    480
ttcaaagaaa accacccgaa tctgtgcgca gtggttaatg atgaaagcga tctgctgaaa    540
cgtggttttg cgagctttgt cgcaagcaac gccaatgccc cgatgcgtaa cgcttttttac   600 gacgcgctga cagcattga ccggtgacc ggtggcggta gcgtgcgcaa tacgttgggc     660
tacaaagtcg gtaataagag cgagttcctg agccagtaca agtttaatct gtgttttgag    720
aacagccaag gctatggtta cgttaccgag aagatcctgg acgcgtactt ctctcacacc    780
attccgatct attggggcag cccgtccgtt gcgaaagact caatccgaa atccttttgtg     840 aatgtccacg acttcaataa ctttgatgag gcgattgatt acattaagta tctgcacacg    900
catccgaatg cgtacttgga catgctgtat gaaaacccgc tgaacaccct ggacggtaag    960
gcgtactttt accaggacct gagcttcaag aaaatcctgg acttttttcaa aaccatcctg   1020 gaaaacgata cgatttacca caagttcagc acgagcttta tgtgggaata tgatttgcat    1080
aagccgctgg ttagcattga cgatctgcgt gtgaattac                           1119

<210> SEQ ID NO 18
<211> LENGTH: 1119
<212> TYPE: DNA
<213> ORGANISM: helicobacter pylori

<400> SEQUENCE: 18
```

```
atgttccaac cactttaga cgcatttatc gagtcggcat caattgagaa aatggcatcg        60
aagagcccgc caccgccgtt gaagatcgcc gtcgctaact ggtggggcga cgaagagatc       120
aaagagttca agaaatctgt gctgtatttc atcctgtccc agcgctatgc gattacgctg       180
caccaaaatc cgaacgagtt cagcgacctg gttctgtcta acccgctggg cgcagcgcgt       240
aagattctga gctaccagaa taccaaacgt gttttctaca ccggtgaaaa cgaaagcccg       300
aacttcaact tgtttgatta cgctatcggt tttgatgaac tggatttcaa tgatcgctat       360
ctgcgtatgc cgctgtacta cgcggagctg cactataaag ccgagcttgt caacgacact       420
accgcgccat ataagctgaa agataatagc ctgtatgcct tgaagaaacc tagccaccac       480
ttcaaagaaa accacccgaa tctgtgcgca gtggttaatg atgaaagcga tctgctgaaa       540
cgtggttttg cgagctttgt cgcaagcaac gccaatgccc cgatgcgtaa cgcttttac        600 gacgcgctga acagcattga ccggtgacc ggtggcggta gcgtgcgcaa tacgttgggc       660
tacaaagtcg gtaataagag cgagttcctg agccagtaca agtttaatct gtgttttgag       720
aacagccaag gctatggtta cgttaccgag aagatcctgg acgcgtactt ctctcacacc       780
attccgatct attggggcag cccgtccgtt gcgaaagact tcaatccgaa atcctttgtg       840
aatgtccacg acttcaataa cttttgatgag gcgattgatt acattaagta tctgcacacg       900
catccgaatg cgtacttgga catgctgtat gaaaacccgc tgaacaccct ggacggtaag       960
gcgtactttt accaggacct gagcttcaag aaaatcctgg acttttcaa aaccatcctg      1020 gaaaacgata cgatttacca caagttcagc acgagctta tgtgggaata tgatttgcat      1080
aagccgctgg ttagcattga cgatctgcgt gtgaattac                            1119

<210> SEQ ID NO 19
<211> LENGTH: 1119
<212> TYPE: DNA
<213> ORGANISM: helicobacter pylori

<400> SEQUENCE: 19
atgttccaac cactttaga cgcatttatc gagtcggcat caattgagaa aatggcatcg        60
aagagcccgc caccgccgtt gaagatcgcc gtcgctaact ggtggggcga cgaagagatc       120
aaagagttca agaaatctgt gctgtatttc atcctgtccc agcgctatgc gattacgctg       180
caccaaaatc cgaacgagtt cagcgacctg gttctgtcta acccgctggg cgcagcgcgt       240
aagattctga gctaccagaa taccaaacgt gttttctaca ccggtgaaaa cgaaagcccg       300
aacttcaact tgtttgatta cgctatcggt tttgatgaac tggatttcaa tgatcgctat       360
ctgcgtatgc cgctgtacta cgcgcatctg cacattaaag ccgagctggt caacgacact       420
accgcgccat ataagctgaa agataatagc ctgtatgcct tgaagaaacc tagccaccac       480
ttcaaagaaa accacccgaa tctgtgcgca gtggttaatg atgaaagcga tctgctgaaa       540
cgtggttttg cgagctttgt cgcaagcaac gccaatgccc cgatgcgtaa cgcttttac        600 gacgcgctga acagcattga ccggtgacc ggtggcggta gcgtgcgcaa tacgttgggc       660
tacaaagtcg gtaataagag cgagttcctg agccagtaca agtttaatct gtgttttgag       720
aacagccaag gctatggtta cgttaccgag aagatcctgg acgcgtactt ctctcacacc       780
attccgatct attggggcag cccgtccgtt gcgaaagact tcaatccgaa atcctttgtg       840
aatgtccacg acttcaataa cttttgatgag gcgattgatt acattaagta tctgcacacg       900
catccgaatg cgtacttgga catgctgtat gaaaacccgc tgaacaccct ggacggtaag       960
```

```
gcgtactttt accaggacct gagcttcaag aaaatcctgg acttttcaa aaccatcctg    1020 gaaaacgata cgatttacca caagttcagc acgagcttta tgtgggaata tgatttgcat    1080
aagccgctgg ttagcattga cgatctgcgt gtgaattac                          1119
```

<210> SEQ ID NO 20
<211> LENGTH: 1119
<212> TYPE: DNA
<213> ORGANISM: helicobacter pylori

<400> SEQUENCE: 20

```
atgttccaac cacttttaga cgcatttatc gagtcggcat caattgagaa aatggcatcg     60
aagagcccgc caccgccgtt gaagatcgcc gtcgctaact ggtggggcga cgaagagatc    120
aaagagttca agaaatttgt gctgtatttc atcctgtccc agcgctatgc gattacgctg    180
caccaaaatc cgaacgagtt cagcgacctg gttctgtcta accgctgggg cgcagcgcgt    240
aagattctga gctaccagaa taccaaacgt gttttctaca ccggtgaaaa cgaaagcccg    300
aacttcaact tgtttgatta cgctatcggt tttgatgaac tggatttcaa tgatcgctat    360
ctgcgtatgc cgctgtacta cgcgcatctg cactataaag ccgagctggt caacgacact    420
accgcgccat ataagctgaa agataatagc ctgtatgcct tgaagaaacc tagccaccac    480
ttcaaagaaa accacccgaa tctgtgcgca gtggttaatg atgaaagcga tctgctgaaa    540
cgtggttttg cgagctttgt cgcaagcaac gccaatgccc cgatgcgtaa cgcttttttac   600 gacgcgctga acagcattga gccggtgacc ggtggcggta gcgtgcgcaa tacgttgggc    660
tacaaagtcg gtaataagag cgagttcctg agccagtaca agtttaatct gtgttttgag    720
aacagccaag gctatggtta cgttaccgag aagatcctgg acgcgtactt ctctcacacc    780
attccgatct attggggcag cccgtccgtt gcgaaagact tcaatccgaa atcctttgtg    840
aatgtccacg acttcaataa cttgatgag gcgattgatt acattaagta tctgcacacg     900
catccgaatg cgtacttgga catgctgtat gaaaacccgc tgaacaccct ggacggtaag    960
gcgtactttt accaggacct gagcttcaag aaaatcctgg acttttcaa aaccatcctg    1020 gaaaacgata cgatttacca caagttcagc acgagcttta tgtgggaata tgatttgcat    1080
aagccgctgg ttagcattga cgatctgcgt gtgaattac                          1119
```

<210> SEQ ID NO 21
<211> LENGTH: 1119
<212> TYPE: DNA
<213> ORGANISM: helicobacter pylori

<400> SEQUENCE: 21

```
atgttccaac cacttttaga cgcatttatc gagtcggcat caattgagaa aatggcatcg     60
aagagcccgc caccgccgtt gaagatcgcc gtcgctaact ggtggggcga cgaagagatc    120
aaagagttca agaaatctgt gctgtatttc atcctgtccc agcgctatgc gattacgctg    180
caccaaaatc cgaacgagtt cagcgacctg gttctgtcta accgctgggg cgcagcgcgt    240
aagattctga gctaccagaa taccaaacgt gttttctaca ccggtgaaaa cgaaagcccg    300
aacttcaact tgtttgatta cgctatcggt tttgatgaac tggatttcaa tgatcgctat    360
ctgcgtatgc cgctgtacta caatgagctg cactataaag ccgagcttgt caacgacact    420
accgcgccat ataagctgaa agataatagc ctgtatgcct tgaagaaacc tagccaccac    480
ttcaaagaaa accacccgaa tctgtgcgca gtggttaatg atgaaagcga tctgctgaaa    540
cgtggttttg cgagctttgt cgcaagcaac gccaatgccc cgatgcgtaa cgcttttttac   600
```

```
gacgcgctga acagcattga gccggtgacc ggtggcggta gcgtgcgcaa tacgttgggc      660
tacaaagtcg gtaataagag cgagttcctg agccagtaca agtttaatct gtgttttgag      720
aacagccaag gctatggtta cgttaccgag aagatcctgg acgcgtactt ctctcacacc      780
attccgatct attggggcag cccgtccgtt gcgaaagact tcaatccgaa atcctttgtg      840
aatgtccacg acttcaataa ctttgatgag gcgattgatt acattaagta tctgcacacg      900
catccgaatg cgtacttgga catgctgtat gaaaacccgc tgaacaccct ggacggtaag      960
gcgtactttt accaggacct gagcttcaag aaaatcctgg actttttcaa aaccatcctg     1020
gaaaacgata cgatttacca caagttcagc acgagcttta tgtgggaata tgatttgcat     1080
aagccgctgg ttagcattga cgatctgcgt gtgaattac                            1119
```

<210> SEQ ID NO 22
<211> LENGTH: 1119
<212> TYPE: DNA
<213> ORGANISM: helicobacter pylori

<400> SEQUENCE: 22

```
atgttccaac cacttttaga cgcatttatc gagtcggcat caattgagaa aatggcatcg       60
aagagcccgc caccgccgtt gaagatcgcc gtcgctaact ggtggggcga cgaagagatc      120
aaagagttca agaaatctgt gctgtatttc atcctgtccc agcgctatgc gattacgctg      180
caccaaaatc cgaacgagtt cagcgacctg gttctgtcta acccgctggg cgcagcgcgt      240
aagattctga gctaccagaa taccaaacgt gttttctaca ccggtgaaaa cgaaagcccg      300
aacttcaact tgtttgatta cgctatcggt tttgatgaac tggatttcaa tgatcgctat      360
ctgcgtatgc cgctgtacta caatcatctg cacattaaag ccgagctggt caacgacact      420
accgcgccat ataagctgaa agataatagc ctgtatgcct tgaagaaacc tagccaccac      480
ttcaaagaaa accacccgaa tctgtgcgca gtggttaatg atgaaagcga tctgctgaaa      540
cgtggttttg cgagctttgt cgcaagcaac gccaatgccc cgatgcgtaa cgcttttttac     600 gacgcgctga acagcattga gccggtgacc ggtggcggta gcgtgcgcaa tacgttgggc      660
tacaaagtcg gtaataagag cgagttcctg agccagtaca agtttaatct gtgttttgag      720
aacagccaag gctatggtta cgttaccgag aagatcctgg acgcgtactt ctctcacacc      780
attccgatct attggggcag cccgtccgtt gcgaaagact tcaatccgaa atcctttgtg      840
aatgtccacg acttcaataa ctttgatgag gcgattgatt acattaagta tctgcacacg      900
catccgaatg cgtacttgga catgctgtat gaaaacccgc tgaacaccct ggacggtaag      960
gcgtactttt accaggacct gagcttcaag aaaatcctgg actttttcaa aaccatcctg     1020
gaaaacgata cgatttacca caagttcagc acgagcttta tgtgggaata tgatttgcat     1080
aagccgctgg ttagcattga cgatctgcgt gtgaattac                            1119
```

<210> SEQ ID NO 23
<211> LENGTH: 1119
<212> TYPE: DNA
<213> ORGANISM: helicobacter pylori

<400> SEQUENCE: 23

```
atgttccaac cacttttaga cgcatttatc gagtcggcat caattgagaa aatggcatcg       60
aagagcccgc caccgccgtt gaagatcgcc gtcgctaact ggtggggcga cgaagagatc      120
aaagagttca agaaatttgt gctgtatttc atcctgtccc agcgctatgc gattacgctg      180
```

| caccaaaatc cgaacgagtt cagcgacctg gttctgtcta acccgctggg cgcagcgcgt | 240 |
| aagattctga ctaccagaa taccaaacgt gttttctaca ccggtgaaaa cgaaagcccg | 300 |
| aacttcaact tgtttgatta cgctatcggt tttgatgaac tggatttcaa tgatcgctat | 360 |
| ctgcgtatgc cgctgtacta caatcatctg cactataaag ccgagctggt caacgacact | 420 |
| accgcgccat ataagctgaa agataatagc ctgtatgcct tgaagaaacc tagccaccac | 480 |
| ttcaaagaaa accacccgaa tctgtgcgca gtggttaatg atgaaagcga tctgctgaaa | 540 |
| cgtggttttg cgagctttgt cgcaagcaac gccaatgccc cgatgcgtaa cgcttttac | 600 |
| gacgcgctga acagcattga gccggtgacc ggtggcggta gcgtgcgcaa tacgttgggc | 660 |
| tacaaagtcg gtaataagag cgagttcctg agccagtaca agtttaatct gtgttttgag | 720 |
| aacagccaag gctatggtta cgttaccgag aagatcctgg acgcgtactt ctctcacacc | 780 |
| attccgatct attggggcag cccgtccgtt gcgaaagact tcaatccgaa atcctttgtg | 840 |
| aatgtccacg acttcaataa ctttgatgag gcgattgatt acattaagta tctgcacacg | 900 |
| catccgaatg cgtacttgga catgctgtat gaaaacccgc tgaacaccct ggacggtaag | 960 |
| gcgtactttt accaggacct gagcttcaag aaaatcctgg actttttcaa aaccatcctg | 1020 |
| gaaaacgata cgatttacca caagttcagc acgagcttta tgtgggaata tgatctgcat | 1080 |
| aagccgctgg ttagcattga cgatctgcgt gtgaattac | 1119 |

<210> SEQ ID NO 24
<211> LENGTH: 1119
<212> TYPE: DNA
<213> ORGANISM: helicobacter pylori

<400> SEQUENCE: 24

| atgttccaac cacttttaga cgcatttatc gagtcggcat caattgagaa aatggcatcg | 60 |
| aagagcccgc caccgccgtt gaagatcgcc gtcgctaact ggtggggcga cgaagagatc | 120 |
| aaagagttca agaaatctgt gctgtatttc atcctgtccc agcgctatgc gattacgctg | 180 |
| caccaaaatc cgaacgagtt cagcgacctg gttctgtcta acccgctggg cgcagcgcgt | 240 |
| aagattctga ctaccagaa taccaaacgt gttttctaca ccggtgaaaa cgaaagcccg | 300 |
| aacttcaact tgtttgatta cgctatcggt tttgatgaac tggatttcaa tgatcgctat | 360 |
| ctgcgtatgc cgctgtacta caatgagctg cacattaaag ccgagcttgt caacgacact | 420 |
| accgcgccat ataagctgaa agataatagc ctgtatgcct tgaagaaacc tagccaccac | 480 |
| ttcaaagaaa accacccgaa tctgtgcgca gtggttaatg atgaaagcga tctgctgaaa | 540 |
| cgtggttttg cgagctttgt cgcaagcaac gccaatgccc cgatgcgtaa cgcttttac | 600 |
| gacgcgctga acagcattga gccggtgacc ggtggcggta gcgtgcgcaa tacgttgggc | 660 |
| tacaaagtcg gtaataagag cgagttcctg agccagtaca agtttaatct gtgttttgag | 720 |
| aacagccaag gctatggtta cgttaccgag aagatcctgg acgcgtactt ctctcacacc | 780 |
| attccgatct attggggcag cccgtccgtt gcgaaagact tcaatccgaa atcctttgtg | 840 |
| aatgtccacg acttcaataa ctttgatgag gcgattgatt acattaagta tctgcacacg | 900 |
| catccgaatg cgtacttgga catgctgtat gaaaacccgc tgaacaccct ggacggtaag | 960 |
| gcgtactttt accaggacct gagcttcaag aaaatcctgg actttttcaa aaccatcctg | 1020 |
| gaaaacgata cgatttacca caagttcagc acgagcttta tgtgggaata tgatttgcat | 1080 |
| aagccgctgg ttagcattga cgatctgcgt gtgaattac | 1119 |

<210> SEQ ID NO 25
<211> LENGTH: 1119
<212> TYPE: DNA
<213> ORGANISM: helicobacter pylori

<400> SEQUENCE: 25

| | | | | | |
|---|---|---|---|---|---|
| atgttccaac | cacttttaga | cgcatttatc | gagtcggcat | caattgagaa | aatggcatcg | 60 |
| aagagcccgc | caccgccgtt | gaagatcgcc | gtcgctaact | ggtggggcga | cgaagagatc | 120 |
| aaagagttca | agaaatttgt | gctgtatttc | atcctgtccc | agcgctatgc | gattacgctg | 180 |
| caccaaaatc | cgaacgagtt | cagcgacctg | gttctgtcta | acccgctggg | cgcagcgcgt | 240 |
| aagattctga | gctaccagaa | taccaaacgt | gttttctaca | ccggtgaaaa | cgaaagcccg | 300 |
| aacttcaact | tgtttgatta | cgctatcggt | tttgatgaac | tggatttcaa | tgatcgctat | 360 |
| ctgcgtatgc | cgctgtacta | caatgagctg | cactataaag | ccgagcttgt | caacgacact | 420 |
| accgcgccat | ataagctgaa | agataatagc | ctgtatgcct | gaagaaacc | tagccaccac | 480 |
| ttcaaagaaa | accacccgaa | tctgtgcgca | gtggttaatg | atgaaagcga | tctgctgaaa | 540 |
| cgtggttttg | cgagctttgt | cgcaagcaac | gccaatgccc | cgatgcgtaa | cgcttttttac | 600 |
| gacgcgctga | acagcattga | gccggtgacc | ggtggcggta | gcgtgcgcaa | tacgttgggc | 660 |
| tacaaagtcg | gtaataagag | cgagttcctg | agccagtaca | agtttaatct | gtgttttgag | 720 |
| aacagccaag | gctatggtta | cgttaccgag | aagatcctgg | acgcgtactt | ctctcacacc | 780 |
| attccgatct | attggggcag | cccgtccgtt | gcgaaagact | tcaatccgaa | atcctttgtg | 840 |
| aatgtccacg | acttcaataa | ctttgatgag | gcgattgatt | acattaagta | tctgcacacg | 900 |
| catccgaatg | cgtacttgga | catgctgtat | gaaaacccgc | tgaacaccct | ggacggtaag | 960 |
| gcgtactttt | accaggacct | gagcttcaag | aaaatcctgg | acttttttcaa | aaccatcctg | 1020 |
| gaaaacgata | cgatttacca | caagttcagc | acgagcttta | tgtgggaata | tgatctgcat | 1080 |
| aagccgctgg | ttagcattga | cgatctgcgt | gtgaattac | | | 1119 |

<210> SEQ ID NO 26
<211> LENGTH: 1119
<212> TYPE: DNA
<213> ORGANISM: helicobacter pylori

<400> SEQUENCE: 26

| | | | | | |
|---|---|---|---|---|---|
| atgttccaac | cacttttaga | cgcatttatc | gagtcggcat | caattgagaa | aatggcatcg | 60 |
| aagagcccgc | caccgccgtt | gaagatcgcc | gtcgctaact | ggtggggcga | cgaagagatc | 120 |
| aaagagttca | agaaatttgt | gctgtatttc | atcctgtccc | agcgctatgc | gattacgctg | 180 |
| caccaaaatc | cgaacgagtt | cagcgacctg | gttctgtcta | acccgctggg | cgcagcgcgt | 240 |
| aagattctga | gctaccagaa | taccaaacgt | gttttctaca | ccggtgaaaa | cgaaagcccg | 300 |
| aacttcaact | tgtttgatta | cgctatcggt | tttgatgaac | tggatttcaa | tgatcgctat | 360 |
| ctgcgtatgc | cgctgtacta | caatcatctg | cacattaaag | ccgagctggt | caacgacact | 420 |
| accgcgccat | ataagctgaa | agataatagc | ctgtatgcct | gaagaaacc | tagccaccac | 480 |
| ttcaaagaaa | accacccgaa | tctgtgcgca | gtggttaatg | atgaaagcga | tctgctgaaa | 540 |
| cgtggttttg | cgagctttgt | cgcaagcaac | gccaatgccc | cgatgcgtaa | cgcttttttac | 600 |
| gacgcgctga | acagcattga | gccggtgacc | ggtggcggta | gcgtgcgcaa | tacgttgggc | 660 |
| tacaaagtcg | gtaataagag | cgagttcctg | agccagtaca | agtttaatct | gtgttttgag | 720 |
| aacagccaag | gctatggtta | cgttaccgag | aagatcctgg | acgcgtactt | ctctcacacc | 780 |

```
attccgatct attggggcag cccgtccgtt gcgaaagact tcaatccgaa atcctttgtg      840
aatgtccacg acttcaataa ctttgatgag gcgattgatt acattaagta tctgcacacg      900
catccgaatg cgtacttgga catgctgtat gaaaacccgc tgaacaccct ggacggtaag      960 gcgtacttt  accaggacct gagcttcaag aaaatcctgg acttttcaa aaccatcctg      1020 gaaaacgata cgatttacca caagttcagc acgagcttta tgtgggaata tgatctgcat      1080
aagccgctgg ttagcattga cgatctgcgt gtgaattac                            1119

<210> SEQ ID NO 27
<211> LENGTH: 1119
<212> TYPE: DNA
<213> ORGANISM: helicobacter pylori

<400> SEQUENCE: 27
atgttccaac cactttttaga cgcatttatc gagtcggcat caattgagaa aatggcatcg      60
aagagcccgc caccgccgtt gaagatcgcc gtcgctaact ggtggggcga cgaagagatc      120
aaagagttca agaaatttgt gctgtatttc atcctgtccc agcgctatgc gattacgctg      180
caccaaaatc cgaacgagtt cagcgacctg gttctgtcta acccgctggg cgcagcgcgt      240
aagattctga gctaccagaa taccaaacgt gttttctaca ccggtgaaaa cgaaagcccg      300
aacttcaact tgtttgatta cgctatcggt tttgatgaac tggatttcaa tgatcgctat      360
ctgcgtatgc cgctgtacta caatgagctg cacattaaag ccgagcttgt caacgacact      420
accgcgccat ataagctgaa agataatagc ctgtatgcct tgaagaaacc tagccaccac      480
ttcaaagaaa accacccgaa tctgtgcgca gtggttaatg atgaaagcga tctgctgaaa      540
cgtggttttg cgagctttgt cgcaagcaac gccaatgccc cgatgcgtaa cgcttttac       600 gacgcgctga acagcattga gccggtgacc ggtggcggta gcgtgcgcaa tacgttgggc      660
tacaaagtcg gtaataagag cgagttcctg agccagtaca agttaatct gtgttttgag      720 aacagccaag gctatggtta cgttaccgag aagatcctgg acgcgtactt ctctcacacc      780
attccgatct attggggcag cccgtccgtt gcgaaagact tcaatccgaa atcctttgtg      840
aatgtccacg acttcaataa ctttgatgag gcgattgatt acattaagta tctgcacacg      900
catccgaatg cgtacttgga catgctgtat gaaaacccgc tgaacaccct ggacggtaag      960 gcgtacttt  accaggacct gagcttcaag aaaatcctgg acttttcaa aaccatcctg      1020 gaaaacgata cgatttacca caagttcagc acgagcttta tgtgggaata tgatctgcat      1080
aagccgctgg ttagcattga cgatctgcgt gtgaattac                            1119
```

HELICOBACTER PYLORI α-1,3 FUCOSYLTRANSFERASE GENE AND PROTEIN WITH IMPROVED SOLUBLE PROTEIN EXPRESSION AND ACTIVITY, AND THEREOF APPLICATION FOR SYNTHESIS OF α-1,3 FUCOSYLOLIGOSACCHARIDE

RELATED APPLICATIONS

The present application is the national phase of International Application No. PCT/KR2015/006272, filed on Jun. 22, 2015, which claims the benefit of priority to Korean Patent Application No. 10-2014-0076720, filed on Jun. 23, 2014, the disclosures of all of which are hereby incorporated herein by reference in their entireties.

TECHNICAL FIELD

The present invention relates to a method of producing a fucosyltransferase mutant by increasing the expression of a soluble protein of *Helicobactor pylori* α-1,3 fucosyltransferase relative to the expression of a difficult-to-express recombinant protein and performing protein engineering via enzyme mutagenesis, and more particularly, to an optimized gene encoding an active fucosyltransferase, an expression vector comprising the gene, a method for expressing the gene, and a method of synthesizing fucosyloligosaccharides using the α-1,3 fucosyltransferase mutant having an increased expression level of soluble protein and increased activity.

BACKGROUND ART

Breast milk provides not only essential nutrients for babies, but also various health benefits that are beyond the mere concept of providing nutrients. Breast milk oligosaccharides are composed of functional components, and have an oligosaccharide content of 5-10 g/liter, which is 100-200 times higher than that of cow's milk. To date, more than 130 kinds of breast milk oligosaccharides were found. The content and structural diversity of these oligosaccharides are very specific in breast milk, unlike the case of cow's milk. Among breast milk oligosaccharides, fucosyloligosaccharides are contained in cow's milk in an amount of less than 1%, but are present in breast milk in a large amount of about 50-80%. Particularly, 3-fucosyllactose, which has lactose at the reducing end and contains fucose linked to glucose by an α-1,3 bond, is not present in cow's milk, but is contained in breast milk in an amount of about 1.0 g/L.

The functions of breast milk fucosyloligosaccharides in the human body are as follows. First, breast milk fucosyloligosaccharides function as prebiotics to promote the growth of useful intestinal microorganisms such as *Lactobacillus* and *Bifidobacteria* while inhibiting the growth of harmful pathogenic microorganisms such as *Clostridium*. These functions are attributable to *Bifidobacteria* that can use short-chain fucosyloligosaccharides as a carbon source. It has been reported that these breast milk fucosyloligosaccharides can maintain the balance of such useful microbial communities, and thus these are effective for the health promotion effects such as prevention or treatment of infectious diseases, exhibition of anticancer activity, stimulation of host immune functions, and show increased vitamin intake.

Second, fucosyloligosaccharides have been studied as inhibitors that inhibit the adhesion of harmful bacteria or viruses to the intestinal epithelial surface of host cells at the initial stage of infection. 3'-Fucosyllactose (Galβ1,4Glc(α-1,3)Fuc) can recognize receptors for *Pseudomonas aeruginosa* which is respiratory tract pathogen, Enterotoxigenic *E. coli, Clostridium, Salmonella fyris*. Thus, these fucosyloligosaccharides can competitively inhibit the invasion of these microorganisms. Breast milk fucosyloligosaccharides, including 3'-fucosyllactose having the above-described function, can be used in various industrial applications, including baby foods, functional foods and medical drugs, etc.

In addition to various breast milk fucosyloligosaccharides, fucose is expressed in the form of sialyl-lewis X (Neu5Ac(α-2,3)Galβ1,4GlcNAc(α-1,3)Fuc) on the surface of leukocytes, and binds to lectin expressed on the surface of epithelial cells, thereby recruiting leukocytes in the initial stage of inflammation. Sialyl-Lewis X having clinical significance in immune response regulation can be used for the treatment of immune-related diseases. For example, in the case in which immune diseases in which the human immune system abnormally induces inflammatory reactions to damage autogenous tissue, sialyl-Lewis X functions as an inhibitor against the binding between leukocytes and lectin, and thus can be used as an anti-inflammatory agent.

If break milk oligosaccharides are extracted from colostrum, there is a disadvantage in that break milk oligosaccharides are difficult to produce in large amounts. In the case of the chemical synthesis of fucosyloligosaccharides, there are problems in that complex protection-deprotection reactions should be performed in order to control the three-dimensional structure of the oligosaccharides and maintain selectivity, and in that toxic reagents should be used. Due to such problems, there is a shortcoming in that it is difficult to be developed into the generalized process used in the food or pharmaceutical industry.

In such terms, synthetic technology based on bioengineering processes has been recognized as the best alternative for the economic production of oligosaccharides, and thus studies thereon have been conducted. Bioengineering processes for the production of fucosyloligosaccharides require the very expensive substrate guanosine 5'-diphosphate fucose (GDP-fuc) as a donor of fucose, and for this reason, studies on the production of guanosine 5'-diphosphate-fucose from guanosine 5'-diphosphate-mannose (GDP-mannose) or fucose and the production of fucosyloligosaccharides using fucosyltransferase have been conducted. It appears that the catalytic ability of fucosyltransferase is very important in order to efficiently transfer fucose from the fucose donor guanosine 5'-diphosphate-fucose to the receptor substrate.

α-1,3 fucosyltransferase that is used in the present invention is an enzyme that transfers fucose to carbon 3-position of glucose or N-acetylglucosamine by an α-1,3 bond, and originates from *Helicobacter pylori* 26695. Bernard Priem et al. removed a cytosine from polyC in accordance with the frame so that active 3-fucosyltransferase would be expressed. In addition, it was found that α-1,3 fucosyltransferase has specificity for substrates, including lactose, N-acetyllactosamine and various oligosaccharides [Claire Dumon, Assessment of the two *Helicobacter pylori* α-1,3-fucosyltransferase ortholog genes for the large-scale synthesis of LewisX human milk oligosaccharides by metabolically engineered *Escherichia coli, Biotechnology Progress,* 2004, 20, pp. 412-9].

It was reported that the C-terminus of α-1,3 fucosyltransferase from *Helicobacter pylori* 26695 has leucine-zipper-like 7-amino-acid repeats, and the substrate specificity of the enzyme varies depending on the number of the repeats.

Meanwhile, for the synthesis of fucosyloligosaccharides, in vivo and in vitro reactions based on both the synthesis of the fucose donor guanosine 5'-diphosphate-fucose and the reaction of fucosyltransferase have been carried out. The fucose donor guanosine 5'-diphosphate-fucose can be produced from L-fucose by the salvage pathway FKP (L-fucokinase/GDP-fucose pyrophosphorylase) enzyme having two enzymatic activities, and fucose can be transferred from the fucose donor to a receptor (e.g., lactose). In the in vivo and in vitro reactions that use the α-1,3 fucosyltransferase, the soluble protein expression level and enzymatic activity of the FKP enzyme in *E. coli* is higher than those of α-1,3 fucosyltransferase. Thus, in these reactions, the fucosyltransferase reaction itself was found to be a rate determining step. To enhance the fucosyltransferase reaction that is a rate determining step, it is highly required to increase the soluble protein expression and enzymatic activity of α-1,3 fucosyltransferase in *E. coli*.

Until now, the total protein expression and soluble protein expression levels of *Helicobacter pylori* α-1,3 fucosyltransferase in *E. coli* have been low, and thus there has been difficulty in that the fucosyltransferase reactions in vivo and in vitro for the synthesis of fucosyloligosaccharides are slow.

α-1,3 fucosyltransferase that is used in the present invention originates from *Helicobacter pylori* 26695, and the C-terminus thereof has two D(D/N)LR(V/I)NY that are leucine-zipper-like 7-amino-acid repeats (heptad repeats). *Helicobacter pylori* α-1,3 fucosyltransferases have 2-10 heptad repeats and α-helix structures at the C-terminus, and all have problems in that the expression level of soluble protein in *E. coli* is very low. For this reason, with respect to α-1,3 fucosyltransferases having 8-10 heptad repeats there has been an attempt to introduce a fusion protein, or to use an expression strain capable of providing rare codon tRNA, or to truncate a portion capable of binding to the cell membrane. However, the expression levels of these α-1,3 fucosyltransferases in *E. coli* still remain at low levels (4-15 mg per L of culture).

The present inventors have attempted to maximize the *E. coli* expression level of soluble protein of the *Helicobactor pylori* 26695 α-1,3 fucosyltransferase having specificity not only for an N-acetylgalactosamine substrate, but also for a lactose substrate.

In order to economically produce large amounts of α-1,3 fucosyloligosaccharide by in vivo or in vitro reactions, it is required to increase enzymatic activity and the expression level of soluble protein in terms of increasing the yield and productivity of the oligosaccharides. 1,3-fucosyltransferase from *Helicobactor pylori* NCTC11639 is the only 1,3-fucosyltransferase whose crystal structure has been determined until now. However, until now, it has been difficult to apply an efficient screening method, due to low soluble protein expression levels. In addition, the mutagenesis on the enzyme, which employs protein engineering mutagenesis has not been attempted. Thus, the present inventors have attempted to identify a mutant having increased enzymatic activity for various receptor substrates, including lactose, compared to a wild-type strain, by use of an α-1,3 fucosyltransferase having an increased expression level of soluble protein.

It is the gist of the present invention to construct an α-1,3 fucosyltransferase mutant, which has an increased amount of soluble protein and increased activity thereof as a result of a change in the terminal structure of the protein, nucleotide sequence substitution and protein engineering mutagenesis for the production of α-1,3 fucosyloligosaccharide, and to increase the yield and productivity of α-1,3 fucosyloligosaccharides by applying the α-1,3 fucosyltransferase mutant for the production of the α-1,3 fucosyloligosaccharides while optimizing enzymatic reactions.

Technical Problem

It is an object of the present invention to provide an α-1,3 fucosyltransferase having an increased expression level of soluble protein and increased activity.

Another object of the present invention is to provide a DNA encoding the α-1,3 fucosyltransferase mutant, a recombinant DNA vector comprising the DNA encoding the α-1,3 fucosyltransferase mutant, a host cell transformed with the recombinant DNA vector, and an extract of the host cell.

Still another object of the present invention is to provide a method for producing α-1,3 fucosyloligosaccharide.

Yet another object of the present invention is to provide a method for producing a fucosyltransferase mutant, and a method for screening a fucosyltransferase mutant.

Technical Solution

The present invention provides a method of increasing the expression level of a soluble protein of α-1,3 fucosyltransferase relative to a difficult-to-express recombinant protein, an active α-1,3 fucosyltransferase protein having an increased expression level, and gene sequence information for an optimized gene encoding the active α-1,3 fucosyltransferase protein.

The present invention also provides a method of expressing the gene in order to maximize the soluble protein expression level of the α-1,3 fucosyltransferase.

The present invention also provides an expression vector comprising an optimized gene that encodes the α-1,3 fucosyltransferase having an increased expression level of soluble protein, and a host cell transformed with a recombinant DNA vector.

The present invention also provides a method of producing α-1,3 fucosyloligosaccharide using the α-1,3 fucosyltransferase having an increased expression level of soluble protein. Specifically, according to the present invention, the yield and productivity of α-1,3 fucosyloligosaccharide is enhanced using the α-1,3 fucosyltransferase having an increased expression level of soluble protein.

The present invention also provides a combined semi-rational method and iterative saturation mutagenesis for producing a fucosyltransferase mutant. The semi-rational method is a combination of directed evolution and rational design methods and is used to ensure only a small number of good-quality mutant libraries. This method comprises selecting a portion targeted by a protein, selecting a specific amino acid residue using the sequence, structure and function of the protein and a computer program, and mutating the selected amino acid residue. In addition, the iterative saturation mutagenesis refers to screening a further improved mutant by mutating another specific amino acid using the mutant, screened by the above method, as a template.

The present invention also provides mutants of SEQ ID NOS: 6, 7, 8 and 9, which result from mutation of a single amino acid in the amino acid sequence of α-1,3 fucosyltransferase; and amino acid sequences of SEQ ID NOS: 10, 11, 12, 13, 14, 15 and 16, which are combinations of the mutants, obtained by iterative saturation mutagenesis. The present invention also provides a fucosyltransferase gene encoding the above mutant, a recombinant DNA vector comprising the gene, and a host cell transformed with the recombinant DNA vector.

The present invention also provides a method of producing α-1,3 fucosyloligosaccharide using α-1,3 fucosyltransferase mutants having an increased expression level of soluble protein and increased activity. Specifically, according to the present invention, the yield and productivity of α-1,3 fucosyltransferase are increased using the *Helicobactor pylori* 26695 α-1,3 fucosyltransferase improved by an increase in the expression level of soluble protein and protein engineering mutagenesis.

Specifically, the present invention provides the following aspects.

The present invention provides an α-1,3 fucosyltransferase mutant represented by any one sequence selected from (a) to (p):

(a) an amino acid sequence of SEQ ID NO: 1;
(b) an amino acid sequence of SEQ ID NO: 2;
(c) an amino acid sequence of SEQ ID NO: 3;
(d) an amino acid sequence having a homology of 95% or more to the amino acid sequence of any one of SEQ ID NOS: 1 to 3 and having fucosyltransferase activity;
(e) a sequence wherein the amino acid at position 128 of any one of SEQ ID NOS: 1 to 3 is substituted with an amino acid other than alanine and aspartic acid;
(f) a sequence wherein the amino acid at position 129 of any one of SEQ ID NOS: 1 to 3 is substituted with an acidic hydrophilic amino acid;
(g) a sequence wherein the amino acid at position 132 of any one of SEQ ID NOS: 1 to 3 is substituted with an amino acid other than tyrosine and histidine;
(h) a sequence wherein the amino acid at position 46 of any one of SEQ ID NOS: 1 to 3 is substituted with a hydrophobic amino acid;
(i) a sequence wherein the amino acid at position 128 of any one of SEQ ID NOS: 1 to 3 is substituted with an amino acid other than alanine and aspartic acid and the amino acid at position 129 is substituted with an acidic hydrophilic amino acid;
(j) a sequence wherein the amino acid at position 128 of any one of SEQ ID NOS: 1 to 3 is substituted with an amino acid other than alanine and aspartic acid and the amino acid at position 132 is substituted with an amino acid other than tyrosine and histidine;
(k) a sequence wherein the amino acid at position 128 of any one of SEQ ID NOS: 1 to 3 is substituted with an amino acid other than alanine and aspartic acid and the amino acid at position 46 is substituted with a hydrophobic amino acid;
(l) a sequence wherein the amino acid at position 128 of any one of SEQ ID NOS: 1 to 3 is substituted with an amino acid other than alanine and aspartic acid, the amino acid at position 129 is substituted with an acidic hydrophilic amino acid, and the amino acid at position 132 is substituted with an amino acid other than tyrosine and histidine;
(m) a sequence wherein the amino acid at position 128 is substituted with an amino acid other than alanine and aspartic acid, the amino acid at position 129 is substituted with an acidic hydrophilic amino acid, and the amino acid at position 46 is substituted with a hydrophobic amino acid;
(n) a sequence wherein the amino acid at position 128 of any one of SEQ ID NOS: 1 to 3 is substituted with an amino acid other than alanine and aspartic acid, the amino acid at position 132 is substituted with an amino acid other than tyrosine and histidine, and the amino acid at position 46 is substituted with a hydrophobic amino acid;

(o) a sequence wherein the amino acid at position 128 of any one of SEQ ID NOS: 1 to 3 is substituted with an amino acid other than alanine and aspartic acid, the amino acid at position 129 is substituted with an acidic hydrophilic amino acid, the amino acid at position 132 is substituted with an amino acid other than tyrosine and histidine, and the amino acid at position 46 is substituted with a hydrophobic amino acid; and (p) a sequence wherein the amino acid at one or more positions selected from the group consisting of positions 128, 129, 132 and 46 of any one of SEQ ID NOS: 1 to 3 is substituted with another amino acid.

The present invention also provides α-1,3 fucosyltransferase mutants represented by SEQ ID NOS: 6 to 16.

The present invention also provides a protein having fucosyltransferase, which comprises a substituted region of an amino acid sequence of any one of SEQ ID NOS: 6 to 16 and has a homology of 75% or more to the amino acid sequence.

The present invention also provides a DNA represented by SEQ ID NO: 4, a DNA having a homology of 77% or more to SEQ ID NO: 4, and DNAs represented by SEQ ID NOS: 17 to 27, which encode α-1,3 fucosyltransferase mutants.

The present invention also provides a recombinant DNA vector comprising the above DNA, a host cell transformed with the recombinant DNA vector, and an extract of the host cell.

The present invention also provides a method for producing 3-fucosyloligosaccharide, wherein either a host cell transformed with the above-described recombinant DNA vector, or an extract of the host cell, is used as a biocatalyst.

The present invention also provides a method for producing an α-1,3 fucosyltransferase mutant, wherein the method comprises the following sequential steps of:

(1) selecting residues or amino acids using any one of the following methods (a) to (e):
(a) a method of selecting residues that are within 5-20 Å from a key amino acid in the crystal structure or model structure of fucosyltransferase;
(b) a method of selecting residues that are within 5-20 Å from amino acid E96, according to method (a);
(c) a method of selecting amino acids, which can cause an evolutionary change in amino acids located in an active site or a substrate access tunnel, from the structure of the protein, according to method (a);
(d) a method of selecting residues that are within 5-20 Å from two substrate binding sites in the crystal structure or model structure of fucosyltransferase; and
(e) a method of selecting amino acids, which can cause an evolutionary change in amino acids located in an active site or a substrate access tunnel, from the structure of the protein, according to method (d); and (2) subjecting the selected residues to iterative saturation mutagenesis, or forming a cluster for the selected residues, thereby obtaining a combinatorial mutant.

The present invention also provides for screening a fucosyltransferase mutant, the method comprising performing a reaction using an indicator that indicates a pH change.

Advantageous Effects

The α-1,3 fucosyltransferase of the present invention, which has a significantly increased soluble protein expression level and activity, can be applied for the production of various high-value-added α-1,3 fucosyloligosaccharides, including not only 3-fucosyllactose that is oligosaccharide derived from a breast milk, but also sialyl-Lewis X.

Specifically, according to the present invention, the amount of enzyme that can be obtained per unit culture of the α-1,3 fucosyltransferase is greatly increased (11 to 50 times), and the unit activity of the enzyme is increased, and thus a material cost associated with the use of the enzyme is reduced. Also, the productivity of fucosyloligosaccharide is increased, and thus the production time is reduced. Also, the production process is improved, and thus the production cost is reduced. In addition, in a reaction employing 5 mM of the donor substrate GDP-fuc, the production yield versus the GDP-fuc concentration is increased to 95-100%. With respect to the efficiency of the substrate, the amount of the product versus the amount of substrate used is increased, indicating that the efficiency of the substrate is significantly increased compared to the prior art. Thus, the economic mass production of fucosyloligosaccharide is possible. In addition, in the mass production of 3-fucosyloligosaccharide, the amount of the receptor substrate that is relatively inexpensive can be increased, and the yield of the product can be increased. Thus, high returns are possible.

Furthermore, the α-1,3 fucosyloligosaccharide can be produced in large amounts, and thus can be used in various applications, including foods and medical drugs.

In addition, through a protein engineering mutagenesis method based on a combined semi-rational method and iterative saturation mutagenesis, the present invention can be applied for not only the production of fucosyltransferase, but also the production of various enzyme mutants.

DESCRIPTION OF DRAWINGS

In FIG. 2, Δ9: deletion of 9 amino acids from a hydrophobic or positively charged, putative α-helix region; Δ45: deletion of 45 amino acids that are a putative α-helix region; Δ52: deletion of 52 amino acids that are a putative α-helix region and one heptad repeat structure; and Δ59: deletion of 59 amino acids that are a putative α-helix region and two heptad repeat structures.

FIG. 3(b) shows the expression levels of total protein and soluble protein after deletion of the C-terminus of the α-1,3 fucosyltransferase, nucleotide sequence optimization and medium optimization.

MODE FOR INVENTION

Figure 1:
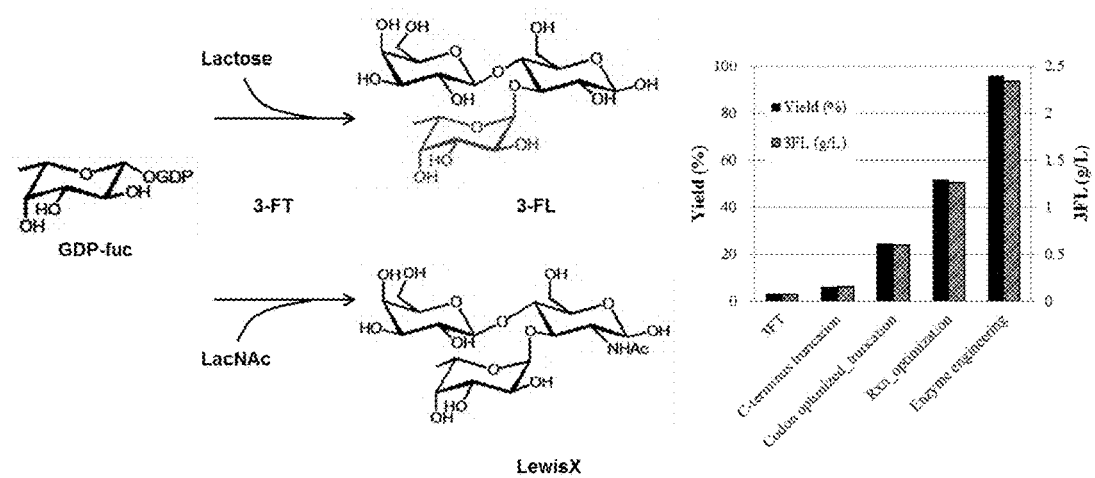
FIG. 1 is a schematic view showing a process of synthesizing α-1,3 fucosyloligosaccharide from guanosine 5'-diphosphate-fucose and a receptor substrate by use of α-1,3 fucosyltransferase, and is a graph showing the increase in production of fucosyloligosaccharide by the present invention.

Terms that are used in the present invention are those that are generally used in the art, and the meaning thereof can be easily understood by any person skilled in the art. The definitions of the terms used herein will now be described in brief.

(1) "Fucosyltransferase" means an enzyme that transfers fucose from the sugar donor guanosine 5'-diphosphate-fucose to a sugar receptor substrate.

(2) Lactose, a receptor substrate, is an oligosaccharide composed of Galβ1,4Glc (galactose and glucose linked to each other by a β1,4 bond). In addition, N-acetyllactosamine, a receptor substrate, is an oligosaccharide composed of Galβ1,4GlcNAc (galactose and N-acetylglucosamine linked to each other by a β1,4 bond).

(3) "α-1,3-fucosyloligosaccharide (3-fucosyloligosaccharide)" means an oligosaccharide comprising fucose linked to a glucose or N-acetylglucosamine moiety by an α-1,3 bond. In addition to glucose or N-acetylglucosamine, other saccharide may further be linked to the oligosaccharide.

(4) "3'-fucosyllactose" means a triose composed of Galβ1,4Glc(α-1,3)Fuc (fucose linked to the glucose of lactose by an α-1,3 bond), and "Lewis K" means a triose composed of Galβ1,4GlcNAc(α-1,3)Fuc (fucose linked to the N-acetylglucosamine of N-acetyllactosamine by an α-1,3 bond).

(5) "Transformation" means introducing external DNA into the host so as to act as a chromosomal element or to be replicable by chromosomal integration.

(6) "Cell extract" means an extract of a microorganism including fucosyltransferase expressed therein.

(7) "Reaction that uses a cell extract" means a reaction that uses a cellular content obtained by lysis of a cell containing a certain enzyme, or a whole cell from which an enzyme had not been separated.

(8) "Protein codon optimization" means changing a nucleotide sequence encoding the amino acid sequence of interest, without changing the amino acid sequence. It is usually used to increase protein expression in a desired host cell. The principle of codon optimization may vary depending on codon usage, the percentage of GC nucleotides in the codon, RNA secondary structure formation, the presence or absence of repeated sequences removal, tRNA preference, etc., and is not limited to any one principle.

(9) "Hydrophilic amino acid" means an amino acid containing in its functional group a high-electronegativity element (oxygen, nitrogen or sulfur) capable of forming a hydrogen bond with water. Examples of the hydrophilic amino acid include serine, threonine, cysteine, tyrosine, aspartic acid, glutamic acid, asparagine, glutamine, histidine, lysine and arginine.

(10) "Acidic amino acid" means an amino acid that has a carboxyl group at its side chain, like aspartic acid or glutamic acid, and that is negatively charged and acidic in a neutral solvent.

(11) "Hydrophobic amino acid" means an amino acid whose side chain is hydrophobic (i.e., has little or no affinity for a water molecule) and whose surface is insoluble in water. Examples of the hydrophobic amino acid include isoleucine, leucine, valine, methionine, phenylalanine, tryptophane, proline, glycine, and alanine.

(12) "PCR" refers to polymerase chain reaction and means a method for specifically amplifying any region of DNA.

(13) "Saturation mutagenesis" means introducing various mutations into a particular position of the nucleotide sequence of a gene. Specifically, "saturation mutagenesis" means inserting an NNK codon in place of the sequence to be mutated, into primers having complementary sequences, which bind to template strands, and inserting mutations into the template by PCR. Herein, N in the NNN or NNK codon represents a nucleotide selected from among A, T, G and C, and K represents a nucleotide selected from among T and G.

(14) "Vector" means a polynucleotide composed of single-stranded, double-stranded, circular or supercoiled DNA or RNA, and may include elements operatively linked at appropriate distances so as to be able to produce a recombinant protein. Such elements may include a replication origin, a promoter, an enhancer, a 5' mRNA leader sequence, a ribosomal binding site, a nucleic acid cassette, termination and polyadenylation sites, and selectable marker sequences, and one or more of these elements may be omitted in specific applications. The nucleic acid cassette can include a restriction enzyme site for insertion of the nucleic acid sequence to be expressed. In a functional vector, the nucleic acid cassette contains the nucleic acid sequence to be expressed including translation initiation and termination sites. If necessary, a vector into which two kinds of cassettes can be inserted may also be used. The above-mentioned functions may additionally be sequenced.

(15) A gene that is inserted into a recombinant DNA vector may be *E. coli* strain BW25113 (DE3) or BL21 (DE3) for expression, etc., but may vary depending on the kind of vector into which the gene is inserted. This vector and expression strain can be easily selected by any person skilled in the art.

(16) "pH indicator" refers to one that is mainly used to determine the neutralization point of titration or to determine the concentration of hydrogen ion (pH). The indicator is divided, according to hydrogen ion index, into an acid form and a base form, which have different colors, and this region is called "discoloration region". The concentration of hydrogen ion based on absorbance can be measured by spectrophotometry.

(17) "Specific activity" means the activity per unit amount of a pure protein from which impurities and other proteins were removed by enzyme purification. The specific activity is expressed as the number of units per mg protein. Herein, one unit is the amount of enzyme that catalyzes the conversion of 1 μmol of a substrate per minute.

Hereinafter, the present invention will be described in further detail.

The present invention provides an α-1,3 fucosyltransferase mutant represented by any one sequence selected from among (a) to (p):

(a) an amino acid sequence of SEQ ID NO: 1;

(b) an amino acid sequence of SEQ ID NO: 2;

(c) an amino acid sequence of SEQ ID NO: 3;

(d) an amino acid sequence having a homology of 95% or more to the amino acid sequence of any one of SEQ ID NOS: 1 to 3 and having fucosyltransferase activity;

(e) a sequence wherein the amino acid at position 128 of any one of SEQ ID NOS: 1 to 3 is substituted with an amino acid other than alanine and aspartic acid;

(f) a sequence wherein the amino acid at position 129 of any one of SEQ ID NOS: 1 to 3 is substituted with an acidic hydrophilic amino acid;

(g) a sequence wherein the amino acid at position 132 of any one of SEQ ID NOS: 1 to 3 is substituted with an amino acid other than tyrosine and histidine;

(h) a sequence wherein the amino acid at position 46 of any one of SEQ ID NOS: 1 to 3 is substituted with a hydrophobic amino acid;

(i) a sequence wherein the amino acid at position 128 of any one of SEQ ID NOS: 1 to 3 is substituted with an amino acid other than alanine and aspartic acid and the amino acid at position 129 is substituted with an acidic hydrophilic amino acid;

(j) a sequence wherein the amino acid at position 128 of any one of SEQ ID NOS: 1 to 3 is substituted with an amino acid other than alanine and aspartic acid and the amino acid at position 132 is substituted with an amino acid other than tyrosine and histidine;

(k) a sequence wherein the amino acid at position 128 of any one of SEQ ID NOS: 1 to 3 is substituted with an amino acid other than alanine and aspartic acid and the amino acid at position 46 is substituted with a hydrophobic amino acid;

(l) a sequence wherein the amino acid at position 128 of any one of SEQ ID NOS: 1 to 3 is substituted with an amino acid other than alanine and aspartic acid, the amino acid at position 129 is substituted with an acidic hydrophilic amino acid, and the amino acid at position 132 is substituted with an amino acid other than tyrosine and histidine;

(m) a sequence wherein the amino acid at position 128 is substituted with an amino acid other than alanine and aspartic acid, the amino acid at position 129 is substituted with an acidic hydrophilic amino acid, and the amino acid at position 46 is substituted with a hydrophobic amino acid;

(n) a sequence wherein the amino acid at position 128 of any one of SEQ ID NOS: 1 to 3 is substituted with an amino acid other than alanine and aspartic acid, the amino acid at position 132 is substituted with an amino acid other than tyrosine and histidine, and the amino acid at position 46 is substituted with a hydrophobic amino acid;

(o) a sequence wherein the amino acid at position 128 of any one of SEQ ID NOS: 1 to 3 is substituted with an amino acid other than alanine and aspartic acid, the amino acid at position 129 is substituted with an acidic hydrophilic amino acid, the amino acid at position 132 is substituted with an amino acid other than tyrosine and histidine, and the amino acid at position 46 is substituted with a hydrophobic amino acid; and (p) a sequence wherein the amino acid at one or more positions selected from the group consisting of positions 128, 129, 132 and 46 of any one of SEQ ID NOS: 1 to 3 is substituted with another amino acid.

The α-1,3 fucosyltransferase mutant according to the present invention can be derived from an α-1,3 fucosyltransferase originating from *Helicobactor pylori* 26695. The α-1,3 fucosyltransferase originating from *Helicobactor pylori* 26695 has its C-terminus two heptad repeats followed by 45 hydrophobic or positively charged amino acids. The two heptad repeats contribute to the dimerization of the α-1,3 fucosyltransferase, and the 45 hydrophobic or positively charged amino acids can form an α-helix structure capable of binding to the cell membrane.

SEQ ID NO: 1 lacks the α-helix structure from the α-1,3 fucosyltransferase originating from *Helicobactor pylori* 26695; SEQ ID NO: 2 lacks the α-helix structure and one heptad repeat; and SEQ ID NO: 3 lacks the α-helix structure and two heptad repeats.

The deletion of the α-helix structure, or the deletion of the α-helix structure and one heptad repeat, or the deletion of the α-helix structure and two heptad repeats from the α-1,3 fucosyltransferase has the effects of increasing the expression of total protein and increasing the expression of soluble protein in the cytosol.

An α-1,3 fucosyltransferase mutant, which has a homology of 95% or more to the amino acid sequences of SEQ ID NOS: 1 to 3 or the amino acid sequence of any one of SEQ ID NOS: 1 to 3 and has fucosyltransferase activity, may be substituted at a particular amino acid position thereof so as to have higher activity.

Amino acid substitution may preferably occur at one or more of positions 128, 129, 132 or 46. For example, two amino acid substitutions may occur at positions 128 and 129, positions 128 and 132, positions 128 and 46, positions 129 and 132, positions 129 and 46, or positions 132 and 46.

The above amino acid positions 128, 129, 132 and 46 are amino acid positions appearing in the enzyme of the present invention. When the sequences of other fucosyltransferases are aligned, the above positions can change, and thus can mean other amino acid positions. In other words, "amino acids at positions 128, 129, 132 and 46" as used herein means amino acids corresponding to positions 128, 129, 132 and 46 of the fucosyltransferase of the present invention.

The amino acid at position 128 is preferably substituted with an amino acid other than alanine and aspartic acid. More preferably, it is substituted with asparagine. In addition, the amino acid sequence of α-1,3 fucosyltransferase is preferably represented by SEQ ID NO: 6 wherein the amino acid at position 128 is substituted with asparagines.

The amino acid at position 129 is preferably substituted with an acidic hydrophilic amino acid. More preferably, it is substituted with glutamic acid. In addition, the amino acid sequence of α-1,3 fucosyltransferase is preferably represented by SEQ ID NO: 7 wherein the amino acid at 129 is substituted with glutamic acid.

The amino acid at position 132 is preferably substituted with an amino acid other than tyrosine and histidine. More preferably, it is substituted with isoleucine. In addition, the amino acid sequence of α-1,3 fucosyltransferase is preferably represented by SEQ ID NO: 8 wherein the amino acid at position 132 is substituted with isoleucine.

The amino acid at position 46 is preferably substituted with a hydrophobic amino acid. More preferably, it is substituted with phenylalanine. In addition, the amino acid sequence of α-1,3 fucosyltransferase is preferably represented by SEQ ID NO: 9 wherein the amino acid at position 46 is substituted with phenylalanine.

The amino acid sequence is also represented by SEQ ID NO: 10, wherein the amino acid at position 128 of SEQ ID NO: 2 is substituted with asparagine and the amino acid at position 129 is substituted with glutamic acid.

The amino acid sequence is also represented by SEQ ID NO: 11 wherein the amino acid at 128 of SEQ ID NO: 2 is substituted with asparagine and the amino acid at position 132 is substituted with isoleucine.

The amino acid sequence is also represented by SEQ ID NO: 12 wherein the amino acid at position 128 of SEQ ID NO: 2 is substituted with asparagine and the amino acid at position 46 is substituted with phenylalanine.

The amino acid sequence is also represented by SEQ ID NO: 13 wherein the amino acid at position 128 of SEQ ID NO: 2 is substituted with asparagine, and the amino acid at position 129 is substituted with glutamic acid, the amino acid at position 132 is substituted with isoleucine.

The amino acid sequence is also represented by SEQ ID NO: 14 wherein the amino acid at position 128 of SEQ ID NO: 2 is substituted with asparagines, the amino acid at position 129 is substituted with glutamic acid, and the amino acid at position 46 is substituted with phenylalanine.

The amino acid sequence is also represented by SEQ ID NO: 15 wherein the amino acid at position 128 of SEQ ID NO: 2 is substituted with asparagines, the amino acid at position 132 is substituted with isoleucine, and the amino acid at position 46 is substituted with phenylalanine.

The amino acid sequence is also represented by SEQ ID NO: 16 wherein the amino acid at position 128 of SEQ ID NO: 2 is substituted with asparagines, the amino acid at position 129 is substituted with glutamic acid, and the amino acid at position 46 is substituted with phenylalanine.

The present invention also provides a DNA encoding the α-1,3 fucosyltransferase mutant.

The DNA may be used without limitation, as long as it is a DNA encoding the amino acid sequence provided according to the present invention. The present invention includes a sequence obtained by optimizing the DNA. The DNA is preferably any one selected from the group consisting of a DNA of SEQ ID NO: 4, a DNA having a homology of 77% or more to SEQ ID NO: 4, and DNAs of SEQ ID NOS: 17 to 27.

The DNA sequence of SEQ ID NO: 4 is a sequence obtained by optimizing a DNA sequence (SEQ ID NO: 5) encoding the amino acid sequence (SEQ ID NO: 2) of α-1,3 fucosyltransferase that lacks the α-helix structure and one heptad repeat. The sequence of SEQ ID NO: 4 has a homology of 76% to the sequence of SEQ ID NO: 5.

The DNA sequence of SEQ ID NO: 17 is a sequence encoding the amino acid sequence of SEQ ID NO: 6.
The DNA sequence of SEQ ID NO: 18 is a sequence encoding the amino acid sequence of SEQ ID NO: 7.
The DNA sequence of SEQ ID NO: 19 is a sequence encoding the amino acid sequence of SEQ ID NO: 8.
The DNA sequence of SEQ ID NO: 20 is a sequence encoding the amino acid sequence of SEQ ID NO: 9.
The DNA sequence of SEQ ID NO: 21 is a sequence encoding the amino acid sequence of SEQ ID NO: 10.
The DNA sequence of SEQ ID NO: 22 is a sequence encoding the amino acid sequence of SEQ ID NO: 11.

The DNA sequence of SEQ ID NO: 23 is a sequence encoding the amino acid sequence of SEQ ID NO: 12.

The DNA sequence of SEQ ID NO: 24 is a sequence encoding the amino acid sequence of SEQ ID NO: 13.

The DNA sequence of SEQ ID NO: 25 is a sequence encoding the amino acid sequence of SEQ ID NO: 14.

The DNA sequence of SEQ ID NO: 26 is a sequence encoding the amino acid sequence of SEQ ID NO: 15.

The DNA sequence of SEQ ID NO: 27 is a sequence encoding the amino acid sequence of SEQ ID NO: 16.

The present invention also provides a recombinant DNA vector comprising the DNA encoding the α-1,3 fucosyltransferase mutant.

The vector may comprise a strong promoter. Examples of the strong promoter include, but are not limited to, trc promoter, tac promoter, T7 promoter, T5 promoter, lac promoter or trp promoter. The use of the strong promoter exhibits the effect of increasing the expression level of soluble protein.

The present invention also provides a host cell transformed with the recombinant DNA vector comprising the DNA encoding the α-1,3 fucosyltransferase mutant, and an extract of the host cell.

The present invention also provides a method of producing 3-fucosyloligosaccharide using the host cell or the extract of the host cell as a biocatalyst. Examples of 3-fucosyloligosaccharide that can be prepared according to the method of the present invention include, but are not limited to, 3-fucosyllactose and Lewis X.

In the method of producing the 3-fucosyloligosaccharide, 0.01-2 mM of an inducer may preferably be used at a temperature between 15° C. and 37° C. When such conditions are satisfied, the effect of increasing the expression of soluble protein is obtained.

As used herein, the term "inducer" means a substance that promotes protein expression. For example, when the lac operon is used, IPTG (isopropyl β-D-1-thiogalactopyranoside) may be used as the inducer; and when the ara operon is used, arabinose may be used as the inducer; and when the trp operon is used, indole acrylic acid may be used as the inducer, but the scope of the present invention is not limited thereto.

In the method of producing the 3-fucosyloligosaccharide, a medium containing a carbon source or a nitrogen source may preferably be used.

The present invention also provides a method for producing 3-fucosyloligosaccharide, wherein a sugar receptor substrate is used at a concentration that is at least two times higher than that of a sugar donor substrate.

The sugar donor is preferably guanosine 5'-diphosphate fucose (GDP-fuc), but is not limited thereto.

The concentration of the sugar receptor substrate is 1.1-20 times, preferably 1.5-10 times, and more preferably 2-5 times the concentration of guanosine 5'-diphosphate-fucose. This concentration conditions enables the economic production of 3-fucosyllactose by increasing the reaction rate of the enzyme and the yield of the product.

The present invention also provides a method for producing an α-1,3 fucosyltransferase mutant, comprising the following sequential steps of:

(1) selecting residues or amino acids using any one of the following methods (a) to (e):

(a) a method of selecting residues that are within 5-20 Å from a key amino acid in the crystal structure or model structure of fucosyltransferase;

(b) a method of selecting residues that are within 5-20 Å from amino acid E96, according to method (a);

(c) a method of selecting amino acids, which can cause an evolutionary change in amino acids located in an active site or a substrate access tunnel, from the structure of the protein, according to method (a);

(d) a method of selecting residues that are within 5-20 Å from two substrate binding sites in the crystal structure or model structure of fucosyltransferase; and (e) a method of selecting amino acids, which can cause an evolutionary change in amino acids located in an active site or a substrate access tunnel, from the structure of the protein, according to method (d); and (2) subjecting the selected residues to iterative saturation mutagenesis, or forming a cluster for the selected residues, thereby obtaining a combinatorial mutant.

As used herein, "amino acid that can cause an evolutionary change" means an amino acid that is not conserved at a particular position of a protein structure and that can be mutated by an evolutionary change from multiple sequence alignments through the sequence information of bioinformatics databases and does not play a direct role in the catalysis of the enzyme.

In addition, "cluster" means a group of portions that form substrate binding sites such as α-helix or β-sheet, which are within 5-20 Å from the substrate binding site of α-1,3 fucosyltransferase.

The present invention also provides for screening a fucosyltransferase mutant prepared by the above-described a method preparing a fucosyltransferase mutant, the method comprising performing a reaction using an indicator that indicates a pH change.

The reaction using the indicator that indicates a pH change may be performed at pH 7-9.

Hereinafter, the present invention will be described in further detail with reference to examples. However, it will be obvious to those skilled in the art that these examples are for illustrative purposes only and are not intended to limit the scope of the present invention.

Increase in Expression Level of Soluble Protein of Fucosyltransferase

In the present invention, it was found that the total protein expression level and soluble protein expression level of the α-1,3 fucosyltransferase from *Helicobactor pylori* 26695 were very low, even though the temperature and the concentration of the inducer IPTG (isopropyl β-D-1-thiogalactopyranoside) were controlled. Thus, it was found that the fucose transfer reaction in the production of fucosyllactose that is a fucosyloligosaccharide is a rate determining step.

Figure 2:
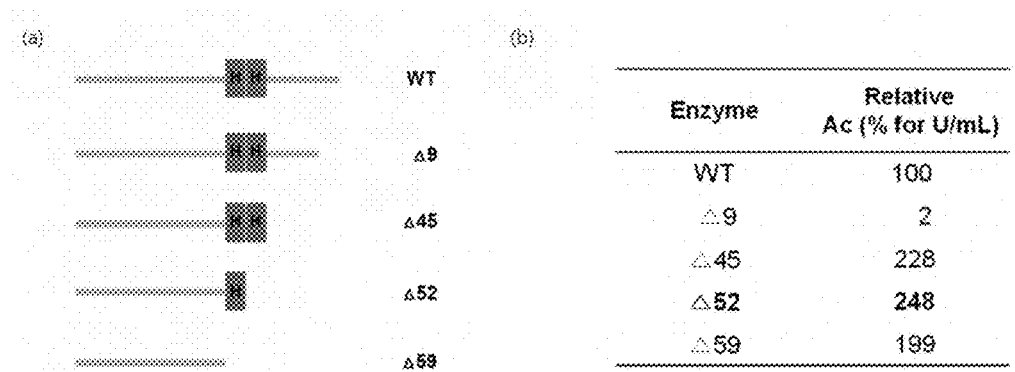
FIG. 2 shows systemic truncation of the C-terminus of the α-1,3 fucosyltransferase according to the present invention (FIG. 2a), and the relative activities of enzymes resulting from the removal of the C-terminus in the production of 3-fucosyllactose (FIG. 2b).

Thus, in order to increase the soluble protein expression level of the α-1,3 fucosyltransferase, as shown in FIG. 2(a), systemic truncation of the C-terminus of the protein, which can form a heptad repeat and an α-helix structure, was performed, and a cell extract of each of the α-1,3 fucosyltransferases having the truncated C-terminus was used to analyze the yield of production of 3-fucosyllactose. As a result, all the α-1,3 fucosyltransferases excluding the C-terminal truncation of 9 amino acids showed an increase in yield of 2-2.5 times compared to the wild-type fucosyltransferase (FIG. 2(b)).

Deletion of a hydrophobic or positively charged putative α-helix portion and a heptad repeat structure can increase the total protein expression level of the α-1,3 fucosyltransferase according to the present invention and can increase the soluble protein expression level of the α-1,3 fucosyltransferase in the cytosol. Specifically, in the α-1,3 fucosyltransferase from *Helicobactor pylori* 26695, an α-1,3 fucosyltransferase lacking the α-helix structure from the C-terminus (SEQ ID NO: 1), an α-1,3 fucosyltransferase lacking the α-helix structure and one heptad repeat (SEQ ID NO: 2), and an α-1,3 fucosyltransferase lacking the α-helix structure and two heptad structures (SEQ ID NO: 3) may be used as an enzyme form that can increase the soluble protein expression level thereof to thereby increase the yield and productivity of 3-fucosyloligosaccharide. Preferably, the α-1,3 fucosyltransferase lacking the α-helix structure, and the α-1,3 fucosyltransferase lacking the α-helix structure and one heptad repeat may be used, and more preferably, the α-1,3 fucosyltransferase lacking the α-helix structure and one heptad repeat may be used.

Figure 3:
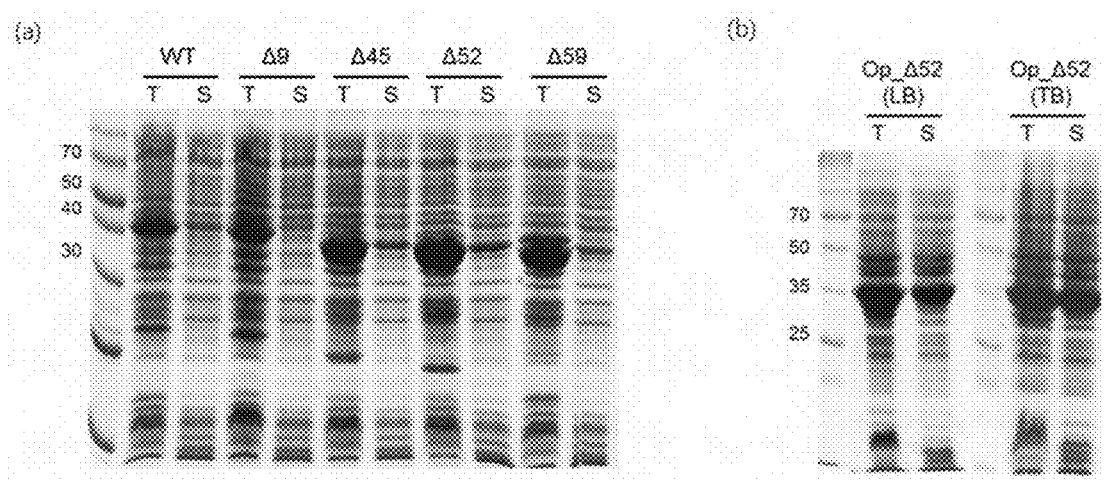
FIG. 3(a) shows total protein (T) and soluble protein (S) for each of the truncated proteins of FIG. 2, obtained by the systemic truncation of the C-terminus of the α-1,3 fucosyltransferase according to the present invention.
FIG. 3(b) shows total protein and soluble protein after nucleotide sequence optimization following the truncation of the C-terminus of the α-1,3 fucosyltransferase. In addition.

As shown in FIG. 3(a), the soluble protein expression level of the C-terminus-truncated α-1,3 fucosyltransferase was increased. In order to further increase the soluble protein expression level, the nucleotide sequence of the C-terminus-truncated α-1,3 fucosyltransferase was optimized. In the present invention, the nucleotide sequence of the α-1,3 fucosyltransferase lacking the α-helix structure and one heptad repeat was optimized by the principle according to which it is substituted with a codon that can maintain acylated tRNA (charged tRNA bound to an amino acid) at a high level (DNA2.0, USA).

A template DNA for nucleotide sequence optimization in the present invention is not limited to the gene encoding the above protein, and a gene encoding a protein lacking the α-helix structure from the C-terminus, and a gene encoding a protein lacking the α-helix structure and two heptad repeats, may also be used.

Figure 4:
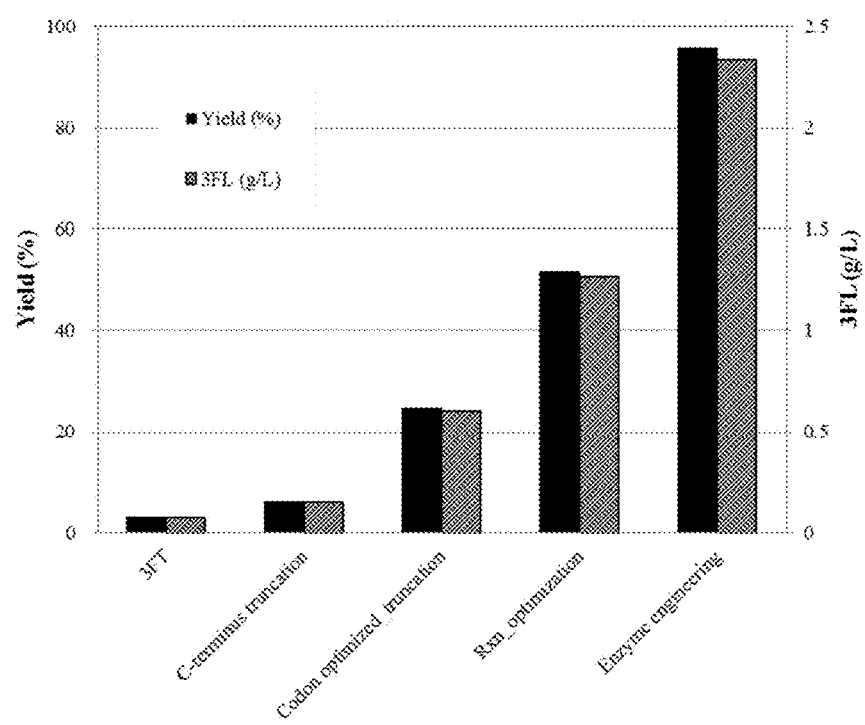
FIG. 4 is a graph showing the increases in the yield (%) and production (g/L) of 3-fucosyllactose by increases in the soluble protein expression level and activity of α-1,3 fucosyltransferase according to the present invention. The yield (%) in the graph indicates the production yield of 3-fucosyllactose as a function of the concentration of guanosine 5'-diphosphate-fucose in the initial stage of enzymatic reactions. "3FT" shows results for an original α-1,3 fucosyltransferase; "C-terminus truncation" shows results for an α-1,3 fucosyltransferase lacking an α-helix structure and one heptad repeat; "codon optimized truncation" shows results for an enzyme obtained by optimization of the nucleotide sequence of the α-helix structure and one heptad repeat; and "Rxn_optimization" shows the results obtained by optimization of the nucleotide sequence of the α-helix structure and one heptad repeat, optimization of a medium for culture of host cells, and optimization of receptor substrate concentration in reactions. In addition, "enzyme engineering" shows the results obtained by mutagenesis on the enzyme via protein engineering of an α-1,3 fucosyltransferase obtained by the above steps and having an increased expression level of soluble protein.

The gene encoding the α-1,3 fucosyltransferase lacking the α-helix structure and one heptad repeat was optimized according to the present invention and expressed in E. coli. As a result, as shown in FIG. 3(b), the total protein expression level and soluble protein expression level thereof significantly increased compared to before optimization. In addition, the yield of the production of 3-fucosyllactose by use of the cell extract increased by about 4 times compared to the use of the cell extract before nucleotide sequence optimization (FIG. 4).

Moreover, when a carbon or nitrogen source such as glycerol and casein hydrolysates is additionally added to a medium for culture of host cells (E. coli) that the α-1,3 fucosyltransferase gene having an optimized nucleotide sequence, it can increase the number of the E. coli cells to thereby further increase the soluble protein expression level per culture. As shown in FIG. 3(b), the expression of total protein can be increased, and the expression level of soluble protein can reach 90% or more of the expression level of total protein. In addition, the yield of α-1,3 fucosyltransferase that can be obtained per liter of E. coli culture is 4-15 mg in previous studies, but was 160-200 mg in the present invention, which is 11 to 50 times higher than that in the previous studies.

Production of Fucosyllactose by Use of α-1,3 Fucosyltransferase Having Increased Expression Level of Soluble Protein Using a cell extract of the α-1,3 fucosyltransferase whose soluble protein level was maximized according to the present invention (FIG. 3(b)), 3-fucosyllactose that is a breast milk α-1,3 fucosyloligosaccharide was produced. In the present invention, reaction conditions were optimized in order to further increase the productivity and yield of 3-fucosyllactose. Specifically, the concentration of the sugar donor substrate guanosine 5'-diphosphate-fucose in sodium phosphate buffer was fixed at 5 mM, and the concentration of the receptor substrate lactose was increased to 10-20 mM, thereby increasing the yield and the reaction rate by at least two times (FIG. 4).

Using 5 mM guanosine 5'-diphosphate-fucose as a substrate, 3-fucosyllactose was produced by the above-described optimized method using a cell extract of the α-1,3 fucosyltransferase whose soluble protein level was maximized. As a result, as shown in FIG. 4, the production yield was increased 52%, and 1.3 g/L of 3-fucosyllactose could be produced. This indicates that the production yield is 17 times higher than the yield of production by use of the initial α-1,3 fucosyltransferase prior to the present invention. In addition, the present invention showed an increase in the productivity of 3-fucosyllactose. Specifically, the α-1,3 fucosyltransferase prior to the present invention showed a productivity of 0.0053 g/L/h in the initial reaction, whereas the present invention showed an increased productivity of 0.63 g/L/h, which corresponds to an increase in productivity of 120 times.

Selection and Mutagenesis of Mutation Targets of α-1,3 Fucosyltransferase

In the present invention, a mutant was produced using as a template protein the α-1,3 fucosyltransferase whose soluble protein level was maximized. For the α-1,3 fucosyltransferase of the present invention, the substrate binding site to which the sugar donor substrate guanosine 5'-diphosphate-fucose was bound was determined using a model structure that uses the crystal structure of other Helicobactor pylori α-1,3 fucosyltransferase as a template. The template protein had a homology of 89% to the α-1,3 fucosyltransferase of the present invention. In the case of the receptor substrate lactose, in order to find the binding site, glutamic acid 96 (E96) that is a key amino acid residue was identified by overlapping with the model structure. With respect to the OH of carbon 3-position of the glucose of lactose from E96, a lactose form that shows stable energy was disposed by the Autodock program, thereby determining the binding site of lactose. The distance between carbon 3-position of the glucose and carbon 1-position of the fucose of guanosine 5'-diphosphate-fucose was measured, and based on the result of the measurement, residues within a distance of 5-20 Å from E96, which can include a distance in which a sugar transfer reaction can occur, were selected.

In the present invention, to select functional residues to be subjected to saturation mutagenesis from among the key amino acid residues, the bioinformatics program "hot spot wizard" was used (Pavelka A., HotSpot Wizard: a web server for identification of hot spots in protein engineering, Nucleic Acids Research, 2009, 37, 376-83). This indicates that amino acids that can cause an evolutionary change in amino acids located in the active site or substrate access tunnel of the protein structure are selected from the protein structure by use of several bioinformatics databases and computer programs. The program performs multiple sequence alignments using sequence information through bioinformatics databases. The mutability of amino acids conserved at particular positions in the protein structure despite evolutionary pressure scores low, because these amino acids play an important role in the structure and function of the protein and are highly likely to play in the catalysis of the protein.

In the present invention, residues having an interaction between the residues selected from the key amino acids and the amino acids determined to have high mutability scores in "hot spot wizard" were selected as mutation targets and subjected to saturation mutagenesis.

Saturation Mutagenesis of Functional Residues of Fucosyltransferase and Production of Mutant by Iterative Saturation Mutagenesis For the functional residues selected as mutation targets, saturation mutagenesis was performed by PCR using an NNK codon, and the mutant libraries were screened by a colorimetric method using a pH indicator. Mutants showing an increased increase in absorbance with time compared to a wild-type strain were screened, and then cultured at an increased culture volume, after which the production yield and initial reaction rate of 3-fucosyllactose by the cell extract were calculated as units per volume (mL) of the cell extract.

A128 selected by the above-described method is located on α-helix around the glucose of the docked lactose. For mutants of A128, mutants substituted with glycine, arginine or glutamic showed activity that was similar to or 20% higher than that of the wild-type strain, and a mutant substituted with asparagines showed an increase in activity of 2.9 times compared to the wild type strain. The specific activities of the A128 mutants were compared with that of the wild-type strain, and as a result, the specific activity of A128N was the highest (190% of that of the wild-type), and the A128N mutant was selected as "hot spot."

The present invention also provides a combined semi-rational method and iterative saturation mutagenesis for producing a fucosyltransferase mutant. The iterative saturation mutagenesis refers to screening a further improved mutant by mutating another specific amino acid using the mutant, screened by the above method, as a template. In the present invention, based on the position of the selected A128 and using the A128N mutant as a template, another certain amino acid was mutated in order to screen a further improved mutant.

Within 5-20 Å around the docked lactose, two α-helixes are present, and the position of residue A128 is present on one of the two helixes. In the present invention, the α-helix including A128 was designated as cluster 1, and the other α-helix was designated as cluster 2. Candidate amino acid for mutation were selected from cluster 1 using the "hot spot wizard", and the selected candidate amino acids were subjected to iterative saturation mutagenesis using the "hot spot" A128N as a template DNA. In addition, candidates for mutation were selected from cluster 2 using the "hot spot wizard", and saturation mutagenesis for each of cluster 1 and cluster 2 was performed.

An additional mutant from A128N of cluster 1 can be produced from a mutant of H129. A H129 mutant substituted with cysteine or serine showed activity similar to that of A128N, and when it was substituted with an acidic hydrophobic amino acid such as glutamic acid or aspartic acid, it showed activity that was two times higher than that of A128N.

An additional mutant from a combinatorial mutant of A128N and H129E/D of cluster 1 can be produced from a mutant of Y132. Y132 can receive relatively diverse mutants, and an Y132 mutant substituted with glycine, serine, glutamic acid, cysteine, valine or the like showed moderate activity, and when it was substituted with a hydrophobic amino acid such as leucine, isoleucine or tryptophan, it showed activity that was 20% higher than that of a combinatorial mutant of A128N and H129E/D.

In addition, a mutant of S46 can be produced from cluster 2 of the present invention. An S46 mutant substituted with threonine showed activity similar to that of the wild-type, and when it was substituted with phenylalanine, it showed an increase in activity of 1.5 times compared to that of the wild-type.

Furthermore, according to the present invention, combinatorial mutants substituted with 3 or 4 amino acids can be produced from cluster 1 and cluster 2. The amino acid mutation of these combinatorial mutants may be A128+H129+Y132, A128+H129+S46, A128+Y132+S46, H129+Y132+S46, or A128+H129+Y132+S46.

In addition, according to the present invention, combinatorial mutants substituted with 2 amino acids can be produced from cluster 1 and cluster 2. The amino acid mutation of these combinatorial mutants may be A128+H129, A128+Y132, A128+S46, H129+Y132, H129+S46, or Y132I+S46.

Characterization of α-1,3 Fucosyltransferase and Application of α-1,3 Fucosyltransferase for Production of Fucosylo-ligosaccharide In the present invention, the single amino acid substitution mutant A128N of A128 of α-1,3 fucosyltransferase has an amino acid sequence of SEQ ID NO: 6, and may include a protein having a sequence wherein the amino acid at position 128 is substituted with any amino acid other than alanine and aspartic acid, and preferably substituted with a hydrophilic amino acid. In addition, other enzymes are also possible, as long as they have a homology of 75% to the above-described mutant sequence having a mutation at position 128 upon alignment with fucosyltransferase and have fucosyltransferase activity. The DNA encoding the protein of SEQ ID NO: 6 is represented by SEQ ID NO: 17, and all DNAs encoding the above amino acid sequence are also possible.

In the present invention, the single amino acid substitution mutant H129E of H129 of α-1,3 fucosyltransferase has an amino acid sequence of SEQ ID NO: 7, and may include a protein having a sequence wherein the amino acid at position 129 is substituted with an acidic hydrophilic amino acid. In addition, other enzymes are also possible, as long as they have a homology of 75% to the above-described mutant sequence having a mutation at position 129 upon alignment with fucosyltransferase and have fucosyltransferase activity. The DNA encoding the protein of SEQ ID NO: 7 is represented by SEQ ID NO: 18, and all DNAs encoding the above amino acid sequence are also possible.

In the present invention, the single amino acid substitution mutant Y132I of Y132 of α-1,3 fucosyltransferase has an amino acid sequence of SEQ ID NO: 8, and may include a protein having a sequence wherein the amino acid at position 132 is substituted with any amino acid other than tyrosine and histidine, and preferably substituted with a hydrophobic amino acid. In addition, other enzymes are also possible, as long as they have a homology of 75% to the above-described mutant sequence having a mutation at position 132 upon alignment with fucosyltransferase and have fucosyltransferase activity. The DNA encoding the protein of SEQ ID NO: 8 is represented by SEQ ID NO: 19, and all DNAs encoding the above amino acid sequence are also possible.

In the present invention, the single amino acid substitution mutant S46F of H129 of α-1,3 fucosyltransferase has an amino acid sequence of SEQ ID NO: 9, and may include a protein having a sequence wherein the amino acid at position 46 is substituted with a hydrophobic amino acid. In addition, other enzymes are also possible, as long as they have a homology of 75% to the above-described mutant sequence having a mutation at position 46 upon alignment with fucosyltransferase and have fucosyltransferase activity. The DNA encoding the protein of SEQ ID NO: 9 is represented by SEQ ID NO: 20, and all DNAs encoding the above amino acid sequence are also possible.

A combinatorial mutant of A128N and H129E of α-1,3 fucosyltransferase has an amino acid sequence of SEQ ID NO: 10, and may include a protein having any amino acid other than alanine and aspartic acid at position 128 or an acidic hydrophilic amino acid at position 129. In addition, other enzymes are also possible, as long as they have a homology of 75% or more to the mutant sequence and have fucosyltransferase activity. The DNA encoding the protein of SEQ ID NO: 10 is represented by SEQ ID NO: 21, and all DNAs encoding the above amino acid sequence are also possible.

A128N of α-1,3 fucosyltransferase can produce a combinatorial mutant with Y132I or S46F, similar to the above-described combinatorial mutant.

A combinatorial mutant of A128N and Y132I of α-1,3 fucosyltransferase has an amino acid sequence of SEQ ID NO: 11, and may include a protein having any amino acid other than alanine and aspartic acid at position 128 or any amino acid sequence other than tyrosine and histidine at position 132. In addition, other enzymes are also possible, as long as they have a homology of 75% or more to the mutant sequence and have fucosyltransferase activity.

A combinatorial mutant of A128N and S46F of α-1,3 fucosyltransferase has an amino acid sequence of SEQ ID NO: 12, and may include a protein having any amino acid other than alanine and aspartic acid at position 128 or a hydrophobic amino acid at position 46. In addition, other enzymes are also possible, as long as they have a homology of 75% or more to the mutant sequence and have fucosyltransferase activity. The DNAs encoding the proteins of SEQ ID NOS: 11 and 12 are represented by SEQ ID NOS: 22 and 23, respectively, and all DNAs encoding the above amino acid sequence are also possible.

A combinatorial mutant of A128N, H129E and Y132 of α-1,3 fucosyltransferase has an amino acid sequence of SEQ ID NO: 13, and may include a protein having any amino acid other than alanine and aspartic acid at position 128 or an acidic hydrophilic amino acid at position 129 or any amino acid sequence other than tyrosine and histidine at position 132. In addition, other enzymes are also possible, as long as they have a homology of 75% or more to the mutant sequence and have fucosyltransferase activity. The DNA encoding the protein of SEQ ID NO: 13 is represented by SEQ ID NO: 24, and all DNAs encoding the above amino acid sequence are also possible.

A combinatorial mutant of A128N, H129E and S46F of α-1,3 fucosyltransferase has an amino acid sequence of SEQ ID NO: 14, and may include a protein having any amino acid other than alanine and aspartic acid at position 128 or an acidic hydrophilic amino acid at position 129 or a hydrophobic amino acid at position 46. In addition, other enzymes are also possible, as long as they have a homology of 75% or more to the mutant sequence and have fucosyltransferase activity. The DNA encoding the protein of SEQ ID NO: 14 is represented by SEQ ID NO: 25, and all DNAs encoding the above amino acid sequence are also possible.

A combinatorial mutant of A128N, Y132I and S46F of α-1,3 fucosyltransferase has an amino acid sequence of SEQ ID NO: 15, and may include a protein having any amino acid other than alanine and aspartic acid at position 128 or any amino acid sequence other than tyrosine and histidine at position 132 or a hydrophobic amino acid at position 46. In addition, other enzymes are also possible, as long as they have a homology of 75% or more to the mutant sequence and have fucosyltransferase activity. The DNA encoding the protein of SEQ ID NO: 15 is represented by SEQ ID NO: 26, and all DNAs encoding the above amino acid sequence are also possible.

A combinatorial mutant of A128N, H129E, Y132I and S46F of α-1,3 fucosyltransferase has an amino acid sequence of SEQ ID NO: 16, and may include a protein having any amino acid other than alanine and aspartic acid at position 128 or an acidic hydrophilic amino acid at position 129 or any amino acid sequence other than tyrosine and histidine at position 132 or a hydrophobic amino acid at position 46. In addition, other enzymes are also possible, as long as they have a homology of 75% or more to the mutant sequence and have fucosyltransferase activity. The DNA encoding the protein of SEQ ID NO: 16 is represented by SEQ ID NO: 27, and all DNAs encoding the above amino acid sequence are also possible.

Examples of sequences having a homology of 75% to the above-described α-1,3 fucosyltransferase mutants include sequences of the genus *Helicobactor*, particularly *Helicobactor* species, which include the mutated sequences of the mutants and are predicted to have α-1,3 fucosyltransferase.

In the present invention, among the above screened α-1,3 fucosyltransferase mutants, single and combinatorial mutants, including A128N, a combinatorial mutant of A128N and H129E (A128N+H129E), a combinatorial mutant of A128N, H129E and Y132I (A128N+H129E+Y132I), and a combinatorial mutant of A128N, H129E and S46F (A128N+H129E+S46F), were selected in order to produce 3-fucosyllactose and Lewis X.

In the production of 3-fucosyllactose in the present invention, the yield of production by use of A128N+H129E, A128N+H129E+Y132I and A128N+H129E+S46F mutants increased to 95% (FIG. 4), which was 31 times higher than the production yield shown by the use of the initial α-1,3 fucosyltransferase whose soluble protein expression level and enzymatic activity were prior to the increase. In addition, these mutants showed a productivity of 2.33 g/L/h, which was 441 times higher than that shown by the initial α-1,3 fucosyltransferase.

Figure 5:
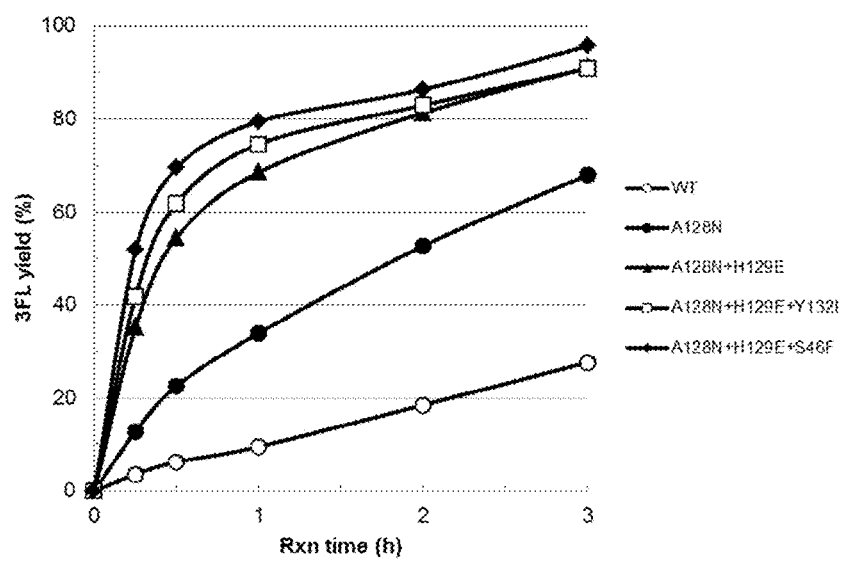
FIG. 5 is a graph showing the yield of production of 3-fucosyllactose by use of each of a wild-type α-1,3 fucosyltransferase and α-1,3 fucosyltransferase mutants according to the present invention. The yield (%) in the graph indicates the production yield of 3-fucosyllactose as a function of the concentration of guanosine 5'-diphosphate-fucose in the initial stage of enzymatic reactions.

In addition, in the present invention, in order to compare the initial reaction rate (U/mL) of the mutants with that of the wild-type, the production yield of 3-fucosyllactose was compared using a cell extract of fucosyltransferase in an amount smaller than that in existing reactions by 50%. FIG. 5 shows the 3-fucosyllactose production yields of the mutants in comparison with that of the wild-type, and as can be seen therein, the initial reaction rate (U/mL) of the A128N+H129E+S46F mutant was 15 times higher than that of the wild-type.

In addition, in the production of Lewis X in the present invention, the yield of production by the A128N+H129E+Y132I and A128N+H129E+S46F mutants increased to 100%, and the mutants showed a productivity of 2.65 g/L/h, which was 4.7 times higher than that of the wild type (0.56 g/L/h).

Figure 6:
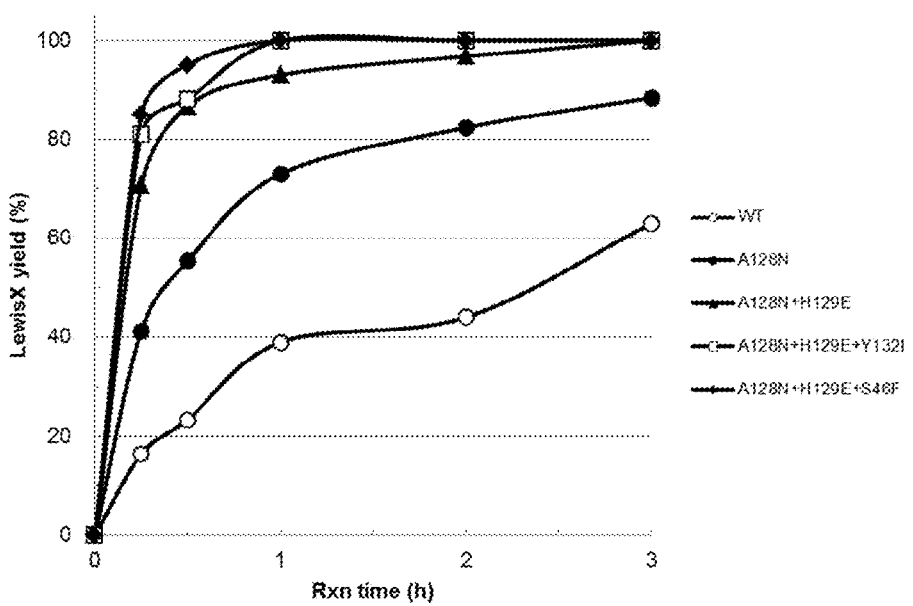
FIG. 6 is a graph showing the yield of production of Lewis X by use of each of a wild-type α-1,3 fucosyltransferase and α-1,3 fucosyltransferase mutants according to the present invention. The yield (%) in the graph indicates the production yield of Lewis X as a function of the concentration of guanosine 5'-diphosphate-fucose in the initial stage of enzymatic reactions.

Moreover, as an example of the use of the mutant in the present invention, in order to compare the initial reaction rate (U/mL) of the mutants with that of the wild type, the production yield of Lewis X was compared using a cell extract of fucosyltransferase in an amount corresponding to 25% of the amount used in existing reactions. FIG. 6 shows the Lewis X production yields of the mutants in comparison with that of the wild type, and as can be seen therein, the initial reaction rate (U/mL) of the A128N+H129E+S46F mutant was 5.2 times higher than that of the wild type.

The α-1,3 fucosyltransferase whose soluble protein expression level and activity were increased according to the present invention may be applied not only for the production of 3-fucosyllactose and Lewis X as described above, but also various α-1,3 fucosyl oligosaccharides, including Lactodifucotetraose (Fuc(α-1,2)Galβ1,4Glc(α-1,3)Fuc), DFpLNnH (Difucosyl-para-lacto-N-neohexaose), LNFP III (Lacto-N- fucopentoseIII), TFLNH (Trifucosyllactose-N-hexose), LNDFH II (Lacto-N-difucohexaose II), and sialyl lewis X).

EXAMPLE 1

Construction of Expression Vector Comprising α-1,3 Fucosyltransferase Gene and Increase in Soluble Protein Expression Level Systemic Truncation of C-terminus of α-1,3 Fucosyltransferase In order to perform systemic truncation of the C-terminus of protein that can form heptad repeat and α-helix structures, a vector cloned with α-1,3 fucosyltransferase was used as a DNA template, and a sense primer having a Nde I restriction enzyme recognition sequence and an antisense primer having a Xho I restriction enzyme recognition sequence were constructed. In all cases, a sense primer of GACCATATGT-TCCAACCCCTATTAG was used. Also, an antisense primer of TCGACTCTCGAGCACCGCGCGCAACAAAGG was used to delete 9 amino acids among the part that can form the α-helix structure of C-terminus. To construct a sequence (SEQ ID NO: 1) lacking 45 amino acids that can form the α-helix structure of C-terminus, an antisense primer of TCGACTCTCGAGATAATTAACCCTCAAATCAT-CATAATTA was used. To construct a sequence (SEQ ID NO: 2) lacking 59 amino acids corresponding to the α-helix structure and one heptad repeat, an antisense primer of TCGACTCTCGAGATAATTAACCCTCAAATCAT-CAATGGAT was used. To construct a sequence (SEQ ID NO: 3) lacking 52 amino acids corresponding to the α-helix structure and two heptad repeats, an antisense primer of TCGACTCTCGAGAATGGATACTAACGGCTT was used. PCR was performed using pfu DNA polymerase after addition of DNA polymerase reaction buffer, 0.2 mM dNTP, 2.5 mM $MgCl_2$, 50-100 ng of the template DNA cloned in a pET vector, and 100 pmol of each of the above-described primers. The PCR was performed under the following conditions: predenaturation at 95° C. for 5 min, and then 30 cycles, each consisting of denaturation at 95° C. for 30 sec, annealing at 55° C. for 1 min and extension at 72° C. for 1 min. Each of the amplified PCR products was treated with the restriction enzymes Nde I and Xho I, and inserted into a pET24ma vector having a T7 promoter. Vectors that are used in the present invention may include all expression vectors having various promoters, including a T7 promoter.

Optimization of Nucleotide Sequence of α-1,3 Fucosyltransferase and Construction of Expression Vector The nucleotide sequence of α-1,3 fucosyltransferase was optimized by the principle according to which it is substituted with a codon that can maintain acylated tRNA (charged tRNA bound to an amino acid) at a high level (DNA2.0, USA). A template DNA for nucleotide sequence optimization may be a gene encoding each of a protein lacking the α-helix structure from the C-terminus, a protein lacking the α-helix structure and one heptad repeat, and a protein lacking the α-helix structure and two heptad repeats.

For example, the optimized nucleotide sequence of the α-1,3 fucosyltransferase lacking the α-helix structure and one heptad repeat is represented by SEQ ID NO: 4, and has a homology of 76% to the original nucleotide sequence (SEQ ID NO: 5.

In addition, the optimized gene encoding the α-1,3 fucosyltransferase lacking the α-helix structure and the heptad repeat was cloned into an expression vector containing a strong promoter by use of Nde I (sense primer) and Xho I (antisense primer), and the C-terminus thereof was tagged with histidine. The strong promoter may be selected from the group consisting of trc promoter, tac promoter, T7 promoter, T5 promoter, lac promoter and trp promoter.

Analysis of Produced Soluble Protein of α-1,3 Fucosyltransferase

The C-terminus of α-1,3 fucosyltransferase that can forms heptad repeat and α-helix structures was truncated, and the α-1,3 fucosyltransferase was cloned into a vector. The recombinant vector cloned with the α-1,3 fucosyltransferase was transformed into an E. coli BW25113 (DE3) strain. Then, the strain was inoculated into an LB medium containing kanamycin antibiotic and was shake-cultured at a temperature of 30 to 37° C. for 5-10 hours. Then, a portion of the culture was inoculated into 50 mL of an LB medium containing 50 μg $mL^{-1}$ of kanamycin antibiotic. The inoculated culture was incubated at a temperature of 30 to 37° C. When the culture reached an $OD_{600}$ of 0.5-1, 0.01-2 mM of IPTG was added thereto, and then the culture was incubated at a temperature of 15 to 37° C. for 15-20 hours to induce protein expression.

In addition, in the case of the α-1,3 fucosyltransferase whose nucleotide sequence was optimized by truncating the C-terminus that can form the heptad repeat and α-helix structures, the α-1,3 fucosyltransferase was inoculated either into LB medium containing kanamycin antibiotic or into TB medium containing glycerol and casein hydrolysates and was shake-cultured at a temperature of 30 to 37° C. for 5 to 10 hours. Then, a portion of the culture was inoculated into 50 mL of an LB or TB medium containing 50 μg $mL^{-1}$ of kanamycin antibiotic. The inoculated culture was incubated at a temperature of 30 to 37° C. When the culture reached an $OD_{600}$ of 0.5-1, 0.01-2 mM of IPTG was added thereto, and then the culture was incubated at a temperature of 15 to 37° C. for 15-20 hours to induce protein expression.

After expression of the α-1,3 fucosyltransferase, the cultured E coil cells were centrifuged at 4000 rpm for 10 minutes, and the cells were recovered, resuspended in distilled water, and then centrifuged again for 10 minutes, followed by removal of the supernatant distilled water. The recovered cell pellet was suspended in 5 mL of 20 mM sodium phosphate buffer and lysed with a sonicator, and the total protein fraction (soluble protein+insoluble aggregate) was collected and centrifuged at 15000 rpm for 30 minutes. Then, the supernatant was separated, thereby obtaining soluble protein. 6 μL each of the total fraction and the soluble protein was mixed with 3 μL of 3×SDS and boiled at 100° C. for 10 minutes. The boiled samples were loaded on 10% acrylamide SDS gels and developed, and then the gels were stained with Coomassie dye, and then decolorized, thereby determining the amount of expressed protein.

EXAMPLE 2

Synthesis of Fucosyllactose Using α-1,3 Fucosyltransferase Whose Soluble Protein Level and Activity was Increased Using the α-1,3 fucosyltransferase whose soluble protein expression level and activity were increased according to the present invention, 3-fucosyllactose and Lewis X were produced using guanosine 5'-diphosphate-fucose as a donor substrate and lactose or N-acetyllactosamine as a receptor substrate.

Under the conditions optimized in order to further increase the productivity and yield of 2'-fucosyllactose, 5 mM guanosine 5'-diphosphate-fucose, 10-20 mM lactose, 5 mM $MgCl_2$ and the α-1,3 fucosyltransferase corresponding to 20% (v/v) of the total reaction volume were allowed to react in 50 mM sodium phosphate buffer at 37° C. It was found that the rate of the reaction was at least two times higher than that of a reaction performed using 5 mM lactose. When the α-1,3 fucosyltransferase whose soluble protein expression level was maximized was used, the production yield increased to 52%, and 1.3 g/L of 3-fucosyllactose could be produced. This indicates that the production yield is 17 times higher than the yield of production by use of the initial α-1,3 fucosyltransferase prior to the present invention. In addition, the α-1,3 fucosyltransferase of the present invention showed an increased productivity of 0.63 g/L/h, which corresponds to an increase in productivity of 120 times (FIG. 4).

In addition, using the mutant having increased activity and derived from the α-1,3 fucosyltransferase whose soluble protein expression level was maximized, 3-fucosyllactose was produced under the above-described conditions. As a result, the production yield of 3-fucosyllactose increased to 95%, and 2.3 g/L of 3-fucosyllactose could be produced. This indicates that the production yield is 31 times higher than the yield of production by use of the initial α-1,3 fucosyltransferase prior to the present invention. In addition, the α-1,3 fucosyltransferase mutant of the present invention showed an increased productivity of 2.33 g/L/h, which corresponds to an increase in productivity of 441 times (FIG. 4).

In addition, in order to compare the activity of the α-1,3 fucosyltransferase mutant having increased activity, a reaction was performed at 37° C. using a cell extract of the mutant in an amount corresponding to 10% (v/v) of the total reaction volume, and the production yield of 3-fucosyllactose was compared. FIG. 5 shows the 3-fucosyllactose production yield of the mutant in comparison with the wild type. Among the mutants, single and combinatorial mutants, including A128N, A128N+H129E, A128N+H129E+Y132I and A128N+H129E+S46F, all showed increased yields and reaction rates compared to the wild type. Among them, the initial reaction rate (U/mL) of the combinatorial mutant A128N+H129E+S46F was 15 times higher than that of the wild type.

In addition, using the α-1,3 fucosyltransferase mutants generated according to the present invention, Lewis X was produced. For the production of Lewis X, 5 mM guanosine 5'-diphosphate-fucose, 5 mM N-acetyllactosamine, 5 mM MgCl$_2$ and the α-1,3 fucosyltransferase cell extract corresponding to 5% (v/v) of the total reaction volume were allowed to react in 50 mM sodium phosphate buffer at 37° C. In the production of Lewis X by use of the α-1,3 fucosyltransferase mutant, the use of the mutants showed an increase in yield of 100% compared to the use of the wild type that showed a yield of 63% in 3 hours of the reaction, and 2.65 g/L of Lewis X in the use of the mutant was produced. FIG. 6 shows the Lewis X production yields of the mutants in comparison with that of the wild type. Among the mutants, single and combinatorial mutants, including A128N, A128N+H129E, A128N+H129E+Y132I and A128N+H129E+S46F, all showed increased yields and reaction rates compared to the wild type. Among them, the initial reaction rate (U/mL) of the combinatorial mutant A128N+H129E+S46F was 5.2 times higher than that of the wild type.

EXAMPLE 3

Screening of Mutant by Saturation Mutagenesis and Colorimetric Method

Using primers introduced with an NNK sequence (N=A, C, G or T, and K=G or T) resulting from substitution of the amino acid at position 128 of α-1,3 fucosyltransferase with any amino acid, vectors were amplified by PCR to construct a library. The α-1,3 fucosyltransferase of the present invention has methionine at position 1 when numbered from the first methionine.

Each of the amplified fucosyltransferase genes comprising the vector sequence was treated with Dpn I enzyme to remove the original plasma, and then transformed into E coil DH5α. Mutated genes were extracted from all the generated colonies and transformed into E coil BW25113 (DE3). Each of the transformed colonies were inoculated into 500 µL of kanamycin-containing TB medium in a 96-well plate and shake-cultured at a temperature of 30 to 37° C. for 18-24 hours. Then, a portion of the culture was inoculated into 500 µL of a fresh TB containing 50 µg mL$^{-1}$ of kanamycin and IPTG (isopropyl β-D-a-thiogalactopyranoside), followed by culture at a temperature of 30 to 37° C. for 15-20 hours. The cultured cells were centrifuged, and the cell pellets were resuspended in 50 µL of BugBuster protein extraction reagent, and centrifuged, and the cell extract was harvested. 10-20 µL of the cell extract was used in a mutant screening reaction. Specifically, the cell extract comprising fucosyltransferase was added to 80-90 µL of a reaction solution containing 1-10 mM Tris buffer (pH 8.0), 1-5 mM guanosine 5'-diphosphate-fucose, 5-10 mM lactose and 0.1-1 mM pH indicator, and the mixture was allowed to react at 37° C. The absorbance of the reaction mixture was measured at intervals of 15 to 30 minutes. The measurement of the activity of fucosyltransferase by a colorimetric method is a method of measuring the change in pH caused by hydrogen ions generated when a glycosidic bond between the fucose donor and the fucose receptor. The activity of fucosyltransferase is proportional to the productivity of fucosyllactose. In the present invention, the decrease in absorbance at 560 nm at which the intensity of the red color of a phenol red indicator decreases was analyzed using a spectrophotometer Korean Patent Application No. 10-2013-0039938).

In the present invention, the screened A128N mutant was used as a "hot spot", and positions 129 and 132 were sequentially subjected to iterative saturation mutagenesis using the above-described method, thereby sequentially producing a combinatorial mutant of A128N and H129E and a combinatorial mutant of A128N, H129E and Y132I. In addition, in the present invention, mutations at amino acid positions 128, 129 and 132 were designated as cluster 1, and a mutation at amino acid position 46 was designated as cluster 2. The clusters were combined to produce a combinatorial mutant of A128N, H129E, Y132I and S46F.

Examples of the combinatorial mutants are not limited to the examples of the present invention, and combinatorial mutants having a substitution of 1, 2, 3 or 4 amino acids can be produced from cluster 1 and cluster 2. In addition, the substituted amino acids are not limited to the examples of the present invention, and substitution with other amino acids is also possible.

The invention claimed is:

1. An α-1,3 fucosyltransferase mutant having any one sequence selected from (a) to (l):
   (a) a sequence wherein the amino acid at position 128 of any one of SEQ ID NOS: 1 to 3 is substituted with asparagine;
   (b) a sequence wherein the amino acid at position 129 of any one of SEQ ID NOS: 1 to 3 is substituted with glutamic acid;
   (c) a sequence wherein the amino acid at position 132 of any one of SEQ ID NOS: 1 to 3 is substituted with isoleucine;
   (d) a sequence wherein the amino acid at position 46 of any one of SEQ ID NOS: 1 to 3 is substituted with phenylalanine;
   (e) a sequence wherein the amino acid at position 128 of any one of SEQ ID NOS: 1 to 3 is substituted with asparagine and the amino acid at position 129 is substituted with glutamic acid;
   (f) a sequence wherein the amino acid at position 128 of any one of SEQ ID NOS: 1 to 3 is substituted with asparagine and the amino acid at position 132 is substituted with isoleucine;
   (g) a sequence wherein the amino acid at position 128 of any one of SEQ ID NOS: 1 to 3 is substituted with asparagine and the amino acid at position 46 is substituted with phenylalanine;
   (h) a sequence wherein the amino acid at position 128 of any one of SEQ ID NOS: 1 to 3 is substituted with asparagine, the amino acid at position 129 is substituted with glutamic acid, and the amino acid at position 132 is substituted with isoleucine;
   (i) a sequence wherein the amino acid at position 128 of any one of SEQ ID NOS: 1 to 3 is substituted with asparagine, the amino acid at position 129 is substituted with glutamic acid, and the amino acid at position 46 is substituted with phenylalanine;

(j) a sequence wherein the amino acid at position 128 of any one of SEQ ID NOS: 1 to 3 is substituted with asparagine, the amino acid at position 132 is substituted with isoleucine, and the amino acid at position 46 is substituted with phenylalanine;

(k) a sequence wherein the amino acid at position 128 of any one of SEQ ID NOS: 1 to 3 is substituted with asparagine, the amino acid at position 129 is substituted with glutamic acid, the amino acid at position 132 is substituted with isoleucine, and the amino acid at position 46 is substituted with phenylalanine; and (l) a sequence wherein the amino acid at one or more positions selected from the group consisting of positions 128, 129, 132 and 46 of any one of SEQ ID NOS: 1 to 3 is substituted with another amino acid, wherein the amino acid at position 128 is substituted with asparagine, the amino acid at position 129 is substituted with glutamic acid, the amino acid at position 132 is substituted with isoleucine, and the amino acid at position 46 is substituted with phenylalanine.

2. The α-1,3 fucosyltransferase mutant of claim 1, having the amino acid sequence of SEQ ID NO: 10 wherein the amino acid at position 128 is substituted with asparagine and the amino acid at position 129 is substituted with glutamic acid.

3. The α-1,3 fucosyltransferase mutant of claim 1, having the amino acid sequence of SEQ ID NO: 11 wherein the amino acid at position 128 is substituted with asparagine and the amino acid at position 132 is substituted with isoleucine.

4. The α-1,3 fucosyltransferase mutant of claim 1, having the amino acid sequence of SEQ ID NO: 12 wherein the amino acid at position 128 is substituted with asparagine and the amino acid at position 46 is substituted with phenylalanine.

5. The α-1,3 fucosyltransferase mutant of claim 1, having the amino acid sequence of SEQ ID NO: 13 wherein the amino acid at position 128 is substituted with asparagine, the amino acid at position 129 is substituted with glutamic acid, and the amino acid at position 132 is substituted with isoleucine.

6. The α-1,3 fucosyltransferase mutant of claim 1, having the amino acid sequence of SEQ ID NO: 14 wherein the amino acid at position 128 is substituted with asparagine, the amino acid at position 129 is substituted with glutamic acid, and the amino acid at position 46 is substituted with phenylalanine.

7. The α-1,3 fucosyltransferase mutant of claim 1, having the amino acid sequence of SEQ ID NO: 15 wherein the amino acid at position 128 is substituted with asparagine, the amino acid at position 132 is substituted with isoleucine, and the amino acid at position 46 is substituted with phenylalanine.

8. The α-1,3 fucosyltransferase mutant of claim 1, having the amino acid sequence of SEQ ID NO: 16 wherein the amino acid at position 128 is substituted with asparagine, the amino acid at position 129 is substituted with glutamic acid, the amino acid at position 132 is substituted with isoleucine, and the amino acid at position 46 is substituted with phenylalanine.

9. A DNA encoding the α-1,3 fucosyltransferase set forth in claim 1.

10. The DNA of claim 9, which has any one sequence selected from (a) to (k):
(a) the DNA sequence of SEQ ID NO: 17;
(b) the DNA sequence of SEQ ID NO: 18;
(c) the DNA sequence of SEQ ID NO: 19;
(d) the DNA sequence of SEQ ID NO: 20;
(e) the DNA sequence of SEQ ID NO: 21;
(f) the DNA sequence of SEQ ID NO: 22;
(g) the DNA sequence of SEQ ID NO: 23;
(h) the DNA sequence of SEQ ID NO: 24;
(i) the DNA sequence of SEQ ID NO: 25;
(j) the DNA sequence of SEQ ID NO: 26; and
(k) the DNA sequence of SEQ ID NO: 27.

11. A recombinant DNA vector comprising the DNA set forth in claim 9 or 10.

12. A method for producing 3-fucosyloligosacchride, wherein either a host cell transformed with the recombinant DNA vector set forth in claim 11, or an extract of the host cell, is used as a biocatalyst.

13. The method for producing 3-fucosyloligosacchride according to claim 12, wherein 0.01 mM -2 mM of an inducer is used at a temperature between 15° C. and 37° C., wherein the inducer is IPTG (isopropyl β-D-1-thiogalactopyranoside), arabinose, or indole acrylic acid.

14. The method for producing 3-fucosyloligosacchride according to claim 12, wherein a sugar receptor substrate is used at a concentration that is at least two times higher than that of a sugar donor substrate.

15. The recombinant DNA vector of claim 11, wherein the vector comprises a strong promoter, wherein the strong promoter is trc promoter, tac promoter, T7 promoter, T5 promoter, lac promoter or trp promoter.

16. A host cell transformed with the recombinant DNA vector of claim 11.

17. The method for producing 3-fucosyloligosacchride of claim 12, wherein a medium supplemented with a carbon source or a nitrogen source is used.

* * * * *